(12) United States Patent
Frampton et al.

(10) Patent No.: US 10,294,253 B2
(45) Date of Patent: May 21, 2019

(54) SILOXANE-CONTAINING PHOSPHOLIPIDS, COMPOSITIONS AND USES THEREOF

(71) Applicants: Mark B. Frampton, Thorold (CA); Paul M Zelisko, Stoney Creek (CA); Drew Marquardt, LaSalle (CA)

(72) Inventors: Mark B. Frampton, Thorold (CA); Paul M Zelisko, Stoney Creek (CA); Drew Marquardt, LaSalle (CA)

(73) Assignees: Mark B. Frampton, Thorold (CA); Paul M. Zelisko, Stoney Creek (CA); Drew Marquardt, LaSalle (CA)

( * ) Notice: Subject to any disclaimer, the term of this patent is extended or adjusted under 35 U.S.C. 154(b) by 0 days.

(21) Appl. No.: 15/618,435

(22) Filed: Jun. 9, 2017

(65) Prior Publication Data

US 2017/0355721 A1   Dec. 14, 2017

Related U.S. Application Data

(60) Provisional application No. 62/348,214, filed on Jun. 10, 2016.

(30) Foreign Application Priority Data

Jun. 10, 2016   (CA) ..................................... 2933001

(51) Int. Cl.
*A61K 9/12*      (2006.01)
*C07F 9/10*      (2006.01)
(Continued)

(52) U.S. Cl.
CPC .............. *C07F 9/10* (2013.01); *A61K 9/1271* (2013.01); *A61K 47/24* (2013.01); *C07F 9/091* (2013.01); *C07F 9/106* (2013.01)

(58) Field of Classification Search
CPC .................................................. A61K 9/1271
See application file for complete search history.

(56) References Cited

U.S. PATENT DOCUMENTS 5,137,660 A       8/1992  Mazur et al.
2015/0259478 A1*  9/2015  Zelisko ..................... C07F 7/21
                                                        524/588

FOREIGN PATENT DOCUMENTS

CA     2106316 A1    9/1992
EP     0292760 A2    11/1988

OTHER PUBLICATIONS

Ruysschaert, Tristan et al., "Liposome retention in size exclusion chromatography", BMC Biotechnology, May 10, 2005, 5:11, doi:10.1186/1472-6750-5-11.

(Continued)

*Primary Examiner* — Benjamin J Packard
(74) *Attorney, Agent, or Firm* — Bereskin & Parr LLP/S.E.N.C.R.L., s.r.l.; Patricia Folkins

(57) ABSTRACT

The present application relates to siloxane-containing phospholipids such as the compounds of Formula I, methods of preparation, compositions and uses thereof.

20 Claims, 5 Drawing Sheets

(51) Int. Cl.
*A61K 9/127* (2006.01)
*A61K 47/24* (2006.01)
*C07F 9/09* (2006.01)

(56) References Cited

OTHER PUBLICATIONS

Shashi, Kant et al., "A Complete Reivew on: Liposomes", International Research Journal of Pharmacy, 2012, 3(7), 10-16.
Kaur, Loveleenpreet et al., "Liposome as a Drug Carrier—A Review", International Journal of Research in Pharmacy and Chemistry, 2013, 3(1), 121-128.
Immordino, Maria Laura et al., "Stealth liposomes: review of the basic science, rationale, and clinical applications, existing and potential", Int. J. Nanomedicine, Sep. 2006, 1(3), 297-315.
Gregoriadis, Gregory, "Engineering liposomes for drug delivery: progress and problems", Elsevier Science Ltd., Tibtech, Dec. 1995 (vol. 13), 527-537.
Krishnamohanrao Kallury, R., et al., "Synthesis of Phospholipids Suitable for Covalent Binding to Surfaces", J. Org. Chem., 1987, 52, 5478-5480.
Zhu, Ling et al,. "Nanoscale Departures: Excess Lipid Leaving the Surface during Supported Lipid Bilayer Formation", Langmuir, 2013, 29, 15283-15292.
Frampton, Mark B., et al., "Chain length selectivity during the polycondensation of siloxane-containing esters and alcohols by immobilized Candida antartica lipase B", Enzyme and Microbial Technology 2014, 58-59, 87-92.
Lei, Q. et al., "Design and synthesis of 1,3-dicapryloyl-2-acetylglycerol as molecular probe for triacylglycerol metabolism study" Eur. J. Lipid Sci. Technol., 2013, 115, 232-238.
Hoffman, D.R et al., "Cytotoxicity and metabolism of alkyl phospholipid analogues in neoplastic cells" Cancer Res., 1986, 46, 5803-5809.
Kim, U.T. et al., "Synthesis of phospholipid headgroups via nucleophilic ring opening of 1,3,2-dioxaphospholanes" J. Chem. Soc., Chem. Commun., 1993, 70-71.
Bhatia, S.K. et al., "Stereospecific synthesis of ether and thioether phospholipids. The use of L-glyceric acid as a chiral phospholipid precursor", J. Org. Chem., 1988, 53, 5034-5039.
Fedotenko, I.A. et al., "The synthesis of 1,3-diamidophospholipids", Tet. Lett., 2010, 51, 5382-5384.
Macintosh, T.J. et al, "Structure and interactive properties of highly fluorinated phospholipid bilayers", Biophysical J., 1996, 71, 1853.
Clary, L. et al., "Polymorphic phase behavior of fluorocarbon double-chain phosphocholines derived from diaminopropanol, serine and ethanolamine and long-term shelf stability of their liposomes", Chem. Phys. Lipids, 1997, 86, 21-35.
Pattni, B.S. et al. "New Developments in Liposomal Drug Delivery", Chemical Reviews, 2015, 115(19), 10938-10966.
Nieh, M.-P. et al., "Controlled release mechanisms of spontaneously forming unilamellar vesicles", Biochim. Biophys. Acta, 2008, 1778, 1467-1471.
Markowski, T. et al., "Highly Asymmetrical Glycerol Diether Bolalipids: Synthesis and Temperature-Dependent Aggregation Behavior", Langmuir, 2015, 31, 10683-10692.
Wang, M. et al.,"Synthesis of mixed-chain phosphatidylcholines including coumarin fluorophores for FRET-based kinetic studies of phospholipase a(2) enzymes", Chem. Phys. Lipids, 2013, 172-173, 78-85.

* cited by examiner

SILOXANE-CONTAINING PHOSPHOLIPIDS, COMPOSITIONS AND USES THEREOF

CROSS-REFERENCE TO RELATED APPLICATIONS

The present application claims the benefit of priority from U.S. provisional application No. 62/348,214 filed on Jun. 10, 2016 and Canadian patent application no. 2,933,001 filed on Jun. 10, 2016, the contents of both of which are incorporated herein by reference in their entirety.

FIELD

The present application relates to siloxane-containing phospholipids, compositions thereof, in particular liposomal compositions thereof, and to their methods of preparation and uses thereof.

BACKGROUND

Phospholipids are a major component of the cellular membrane and participate in the regulation of cellular functions, act as second messengers, and as substrates for phospholipases, lipid kinases, and phosphatases. Once thought to merely house protein machinery, phospholipids are now known to participate in the regulation of cellular and sub-cellular biochemical functions such as membrane trafficking, regulating membrane proteins, and creating sub-cellular compartments which contribute to overall cellular functioning.[1,2]

Nature has evolved a diverse library of phospholipids and lipidomic analyses have identified the existence of several, structurally different lipid types existing within a single cell.[2] Lipid architecture is generally derived from a glycerol backbone to which several different fatty acids and phosphate head groups can be appended to generate a large library of lipids.

Phospholipids present three distinct regions where chemical modifications allow for the generation non-natural lipid molecules. The hydrophilic phosphate head group can be linked to one of several moieties such as choline, ethanolamine, glycerol, inositol, or serine. Lipid head groups have been shown to direct lipids to either the external or cytosolic leaflet of the plasma membrane.[2]

Modification of the head group through tethering polyethylene glycol oligomers (PEGylation) has been used to tune the hydrophilicity of the head group and results in reducing or eliminating enzymatic hydrolysis and promotes extended circulation times of lipid nanoparticles in vivo.[3]

The glycerol backbone of phospholipids presents another potential location for chemical modification. In nature, changing of the ester linkage to that of an ether (or an enyl linkage) has biological implications. For example, 1-alkyl-glycerophosphocholines have been implicated as anti-hypertensive agents[4], and play a role as selective cytotoxic agents in some human cancer cell lines.[5,6] Stereospecific methods have been developed to produce libraries of ether and thioether lipids[7] as well as amide-derived lipids.[8]

The fatty acid chains of lipids presents a further location in which modifications can be incorporated, for example, which tune the hydrophobic character of the lipid. The incorporation of short fluorinated segments into the fatty acid (FA) tails has been disclosed to provide higher stability and longer circulation times for lipid nanoparticles in vivo.[9,10] The introduction of a single fluorine into the myristic acid 1,2-dimyristoyl-sn-3-glycerolphosphocholine (DMPC) chains was observed to not interrupt overall lipid order or the phase transition temperature.[11,12] Asymmetric bolaphospholipids featuring ether linkages have been synthesized and their self-assembly behaviour studied.[13] Modifications to the FA chains are commonly introduced to incorporate fluorophores enabling phospholipase kinetic experiments to be performed.[14]

Krishnamohanrao et al. prepared two asymmetric phosphocholines in which one of the chains was modified with a chlorodimethylsiloxy group (Scheme 1).[15]

Scheme 1

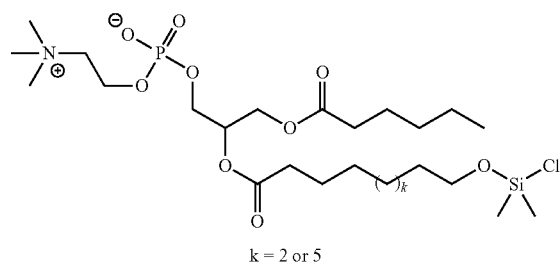

k = 2 or 5

EP 0292760 reports the preparation of linear and cyclic alkylpolysiloxanes having the following general formulae I and II:

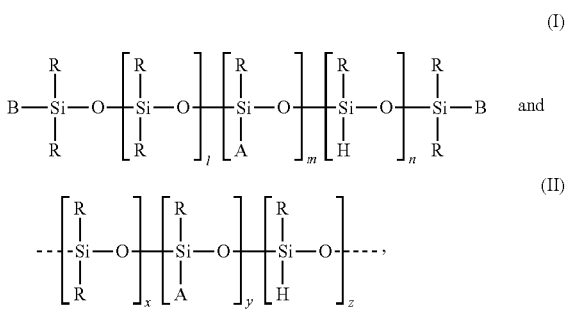

wherein each R is an alkyl radical and A is an organic group having the general formula:

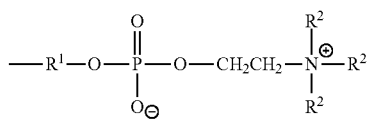

wherein $R^1$ is an alkylene group containing 3 to 50 carbon atoms, $R^2$ is selected from hydrogen atoms and an alkyl group containing 1 to 25 carbon atoms, B is selected from the group R, hydrogen atoms and the group A, with the proviso that there is at least one A group in the molecule.

Phospholipids with long chain fatty acid tails (>10 carbons) self-assemble into multilamellar vesicles (MLVs) in aqueous solutions. Unilamellar vesicles (ULVs) differ from MLVs in that circulation times can be extended, making ULVs better suited as delivery vehicles. From a delivery perspective small ULVs, ranging in size from 50-150 nm and with low size polydispersity, are desirable. Current methods for preparing ULVs include sonication or tedious extrusion procedures which can be time consuming and require expensive specialized equipment.[16] Spontaneous vesicle formation has been observed previously and vesicles formed in this manner may be useful for drug delivery.[17]

SUMMARY

New siloxane phosphocholines have been synthesized and their aggregates characterized in aqueous solution. The siloxane phosphocholines form nearly monodisperse vesicles without the need for secondary extrusion processes. The area/lipid, lipid volume and bilayer thickness were determined from small angle x-ray scattering experiments.

Accordingly, the present application includes a compound of formula I:

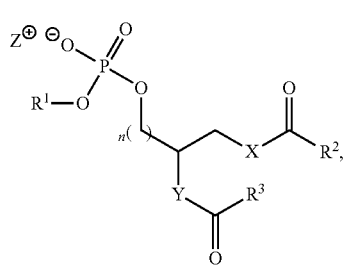

wherein
$R^1$ is a phospholipid head group;
$R^2$ and $R^3$ are independently selected from $C_{2-30}$alkylene-A and $C_{2-30}$alkenylene-A;
A has the structure:

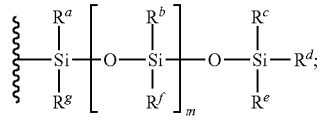

$R^a$, $R^b$, $R^c$, $R^d$, $R^e$, $R^f$ and $R^g$ are independently selected from $C_{1-6}$alkyl, $C_{3-10}$cycloalkyl, $C_{1-6}$alkylene$C_{6-10}$aryl and $C_{6-10}$aryl;
m is an integer of from 0 to 20;
n is 0 or 1;
X is selected from O and $NR^4$;
Y is selected from O, $NR^4$ and $CH_2$—O;
$R^4$ is H or $C_{1-4}$alkyl; and
$Z^+$ is a counter cation or $Z^+$ is not present when $R^1$ is a phospholipid head group comprising a counter cation.

The present application also includes a method of preparing liposomes comprising subjecting an aqueous dispersion of one or more compounds of the application to one or more cycles wherein each cycle comprises freezing, thawing and mechanical agitation, to provide an aqueous suspension of liposomes comprising the one or more compounds.

The present application also includes liposomes comprising one or more compounds of the application.

The present application also includes a pharmaceutical composition comprising liposomes of the application and a pharmaceutically acceptable carrier. In some embodiments, the liposomes further comprise an agent. In some embodiments, the agent is encapsulated within the liposomes. In some embodiments, the encapsulation of the agent within the liposomes is faster than with liposomes prepared using non-siloxane containing phospholipids.

The present application further includes an active agent delivery system comprising the liposomes of the application.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The present application will now be described in greater detail with reference to the drawings in which.

DETAILED DESCRIPTION

I. Definitions

Figure 1:
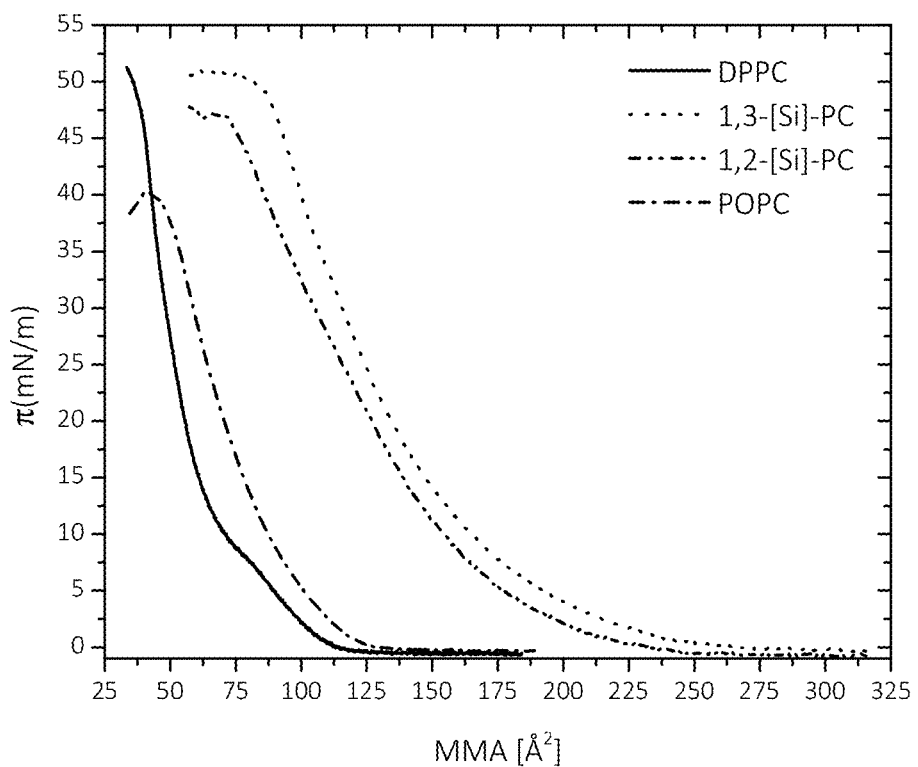
FIG. 1 shows the Langmuir isotherms of two silicon-containing phosphocholines (SiPCs), 1,2-dipalmitoyl-sn-3-phosphocholine (DPPC), and 1-palmitoyl-2-oleoyl-sn-3-phosphocholine (POPC) at 21.5° C. as exemplary and comparative embodiments of the present application.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds. In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions for the reaction to proceed to a sufficient extent to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The compounds of the present application may further exist in varying polymorphic forms and it is contemplated that any polymorphs which form are included within the scope of the present application.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds having alternate stereochemistry.

The term "alkyl" as used herein, whether it is used alone or as part of another group, means straight or branched chain, saturated alkyl groups. The term $C_{1-6}$alkyl means an alkyl group having 1, 2, 3, 4, 5 or 6 carbon atoms.

The term "alkylene" as used herein means straight or branched chain, saturated alkylene group, that is, a saturated carbon chain that contains substituents on two of its ends. The term $C_{1-6}$alkylene means an alkylene group having 1, 2, 3, 4, 5 or 6 carbon atoms.

The term "alkenyl" as used herein, whether it is used alone or as part of another group, means straight or branched chain, unsaturated alkenyl groups. The term $C_{2-6}$alkenyl means an alkenyl group having 2, 3, 4, 5 or 6 carbon atoms and at least one double bond, for example 1-3, 1-2 or 1 double bond.

The term "alkenylene" as used herein means straight or branched chain, unsaturated alkenylene group that is an unsaturated carbon chain that contains substituents on two of its ends. The term $C_{2-6}$alkenylene means an alkenylene group having 2, 3, 4, 5 or 6 carbon atoms and at least 1, for example 1-3, 1-2 or 1 double bond.

The term "cycloalkyl" as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to cyclic groups containing 6 to 10 carbon atoms that contain at least one aromatic ring. In an embodiment of the application, the aryl group contains 6, 9 or 10 carbon atoms, such as phenyl, naphthyl or indanyl.

The term "liposome" refers herein to a spherical vesicle bounded by at least one bilayer of an amphiphilic siloxane-containing phospholipid. The liposomes are either multilamellar vesicles (MLVs or having more than one lipid bilayer) or unilamellar vesicles (ULVs, having only one lipid bilayer).

The term "unilamellar vesicles (ULVs)" is defined herein as a spherical vesicle bounded by a single lipid bilayer. Small unilamellar vesicles (SUVs) have an average diameter size ranging up to 100 nm, large unilamellar vesicles (LUVs) have sizes more than 100 nm up to few micrometers and giant unilamellar vesicles (GUVs) have an average diameter of 100 µm.

The terms "encapsulated" or "encapsulation" as used herein means that the referred-to agent is located inside, or in the internal phase or core of, the liposome.

The term "counter cation" as used herein refers to a positively charged species consisting of a single element, or a positively charged species consisting of a group of elements connected by ionic and/or covalent bonds. The counter cation can be either inorganic or organic in nature and can be a separate species (intermolecular) or be included as part of the same molecule (intramolecular).

The term "compound(s) of the application" as used herein refers to one or more compounds of Formula I.

The term "liposomes of the application" as used herein refers to liposomes in which a bilayer surface comprises one or more compounds of Formula I.

The term "phospholipid headgroup" as used herein refers to any functional grouping that is comprised in the hydrophilic portion of a phospholipid and is generally the functional group attached to the phosphate.

The term "polydispersity index" or "PDI" as used herein is a dimensionless number that is related to the size distribution of particles in a solution. PDI can be obtained by analysis of correlation data measured with the technique known as dynamic light scattering. This index is a number calculated from a simple two parameter fit to the correlation data (the cumulants analysis). The PDI is dimensionless and scaled such that values smaller than 0.05 are rarely seen other than with highly monodisperse standards. Values greater than 0.7 indicate that the sample has a very broad size distribution and is probably not suitable for size distribution measurement by dynamic light scattering (DLS) technique. The various size distribution algorithms work with data that falls between these two extremes. The calculations for these parameters are defined in the ISO standard document 13321:1996 E and ISO 22412:2008.

The term "pharmaceutically acceptable" as used herein means compatible with the treatment of subjects, for example humans.

The term "pharmaceutically acceptable carrier" as used herein means a non-toxic solvent, dispersant, excipient, adjuvant or other material which is mixed with an agent in order to permit the formation of a pharmaceutical composition: i.e., a dosage form for administration to a subject.

The term "agent" as used herein refers to any substance which one wishes to encapsulate in, attach to or combine with the liposomes of the present application. Typically the agent will be a biologically active agent or a drug, and includes, for example, small organic molecules, small inorganic molecules, oligonucleotides, sugars, carbohydrates, proteins, peptides and lipids.

The term "aqueous solution" as used herein means a solution wherein the solvent is primarily water, although small amounts, for example, less than 10, 9, 8, 7, 6, 5, 4, 3, 2 or 1% (v/v) of a non-aqueous solvent may be present.

II. Compounds

Nature provides a broad library of phospholipids that are responsible for providing a barrier between the internal and external cellular environments as well as participating in other biochemical roles. Phospholipids and other lipid-like molecules have the capacity to self-assemble into varying liposomal architectures. Phospholipid-based liposomes are useful, for example, as delivery vehicles. Both traditional chemistry and biocatalysis were used to synthesize trisiloxane-containing phosphocholines (SiPCs). Small angle X-ray scattering (SAXS) data indicated that, unlike their diacyl phosphocholine analogs, SiPCs do not self-assemble into multilamellar vesicles in aqueous solution, instead forming unilamellar vesicles without the need for numerous extrusion sequences. Dynamic light scattering measurements (DLS) revealed that the resulting unilamellar liposomal systems ranged from 100-200 nm in diameter.

Accordingly, the present application includes a compound of formula I:

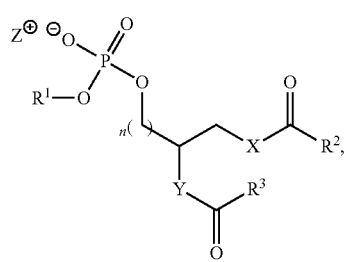

(I)

wherein $R^1$ is a phospholipid head group;

$R^2$ and $R^3$ are independently selected from $C_{2-30}$alkylene-A and $C_{2-30}$alkenylene-A;

A has the structure:

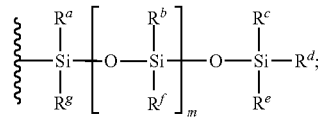

$R^a$, $R^b$, $R^c$, $R^d$, $R^e$, $R^f$ and $R^g$ are independently selected from $C_{1-6}$alkyl, $C_{3-10}$cycloalkyl, $C_{1-6}$alkylene$C_{6-10}$aryl and $C_{6-10}$aryl;

m is an integer of from 0 to 20;

n is 0 or 1;

X is selected from O and $NR^4$;

Y is selected from O, $NR^4$ and $CH_2$—O;

$R^4$ is H or $C_{1-4}$alkyl; and $Z^+$ is a counter cation or $Z^+$ is not present when $R^1$ is a phospholipid head group comprising a counter cation.

In some embodiments, $R^1$ is selected from choline, inositol, ethanolamine, serine, glycerol, phosphotidic acid, and polyethylene glycol (PEG) modified derivatives thereof. In some embodiments, $R^1$ is selected from choline, inositol, ethanolamine, serine and glycerol. In some embodiments, $R^1$ is choline.

In some embodiments, $R^2$ and $R^3$ are independently $C_{2-20}$alkylene-A. In some embodiments, $R^2$ and $R^3$ are independently $C_{2-10}$alkylene-A. In some embodiments, $R^2$ and $R^3$ are independently $C_{6-20}$alkylene-A. In some embodiments, $R^2$ and $R^3$ are independently $C_{6-15}$alkylene-A. In some embodiments, $R^2$ and $R^3$ are independently $C_{6-10}$alkylene-A. In some embodiments, $R^2$ and $R^3$ are independently $C_{7-9}$alkylene-A.

In some embodiments, $R^2$ and $R^3$ are independently $C_{2-20}$alkenylene-A. In some embodiments, $R^2$ and $R^3$ are independently $C_{2-10}$alkenylene-A. In some embodiments, $R^2$ and $R^3$ are independently $C_{6-20}$alkenylene-A. In some embodiments, $R^2$ and $R^3$ are independently $C_{6-15}$alkenylene-A. In some embodiments, $R^2$ and $R^3$ are independently $C_{6-10}$alkenylene-A. In some embodiments, $R^2$ and $R^3$ are independently $C_{7-9}$alkenylene-A.

In some embodiments, $R^a$, $R^b$, $R^c$, $R^d$, $R^e$, $R^f$ and $R^g$ are independently selected from $C_{1-4}$alkyl, $C_{4-6}$cycloalkyl, $C_{1-4}$alkylene$C_{6-10}$aryl and $C_{6-10}$aryl. In some embodiments, $R^a$, $R^b$, $R^c$, $R^d$, $R^e$, $R^f$ and $R^g$ are independently selected from $C_{1-4}$alkyl. In some embodiments, $R^a$, $R^b$, $R^c$, $R^d$, $R^e$, $R^f$ and $R^g$ are independently selected from methyl, ethyl, n-propyl, isopropyl, n-butyl, sec-butyl, isobutyl, tert-butyl, cyclobutyl, cyclopentyl, cyclohexyl, benzyl and phenyl. In some embodiments, $R^a$, $R^b$, $R^c$, $R^d$, $R^e$, $R^f$ and $R^g$ are the same. In some embodiments, $R^a$, $R^b$, $R^c$, $R^d$, $R^e$, $R^f$ and $R^g$ are each methyl.

In some embodiments, m is an integer of from 0 to 10. In some embodiments, m is an integer of from 0 to 5. In some embodiments, m is an integer of from 0 to 4. In some embodiments, m is an integer of from 0 to 3. In some embodiments, m is an integer of from 0 to 2. In an embodiment, m is 1.

In some embodiments, X is O. In some embodiments, X is $NR^4$.

In some embodiments, Y is $NR^4$. In some embodiments, Y is selected from O and $CH_2$—O. In some embodiments, Y is O. In some embodiments, Y is $CH_2$—O.

In some embodiments, $Z^+$ is selected from an inorganic or organic species. In some embodiments, $Z^+$ is an inorganic species. In some embodiments, the inorganic species is a metal. In some embodiments, suitable metal species include, for example alkali metals, lithium ($Li^+$), sodium ($Na^+$) and potassium ($K^+$); alkaline earth metals, beryllium ($Be^{+2}$), magnesium ($Mg^{+2}$), calcium ($Ca^{+2}$), strontium ($Sr^{+2}$) and barium ($Ba^{+2}$); amphoteric metal ions, aluminum ($Al^{+3}$), gallium ($Ga^{+3}$), germanium ($Ge^{+3}$), tin ($Sn^{+4}$) and lead ($Pb^{+2}$ and $Pb^{+4}$); and transition metals, titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{4}$), osmium ($Os^{+2}$, $Os^{+3}$ and $Os^{+4}$), iridium ($Ir^{+2}$, $Ir^{+3}$ and $Ir^{+4}$), mercury ($Hg^{+2}$) and bismuth ($Bi^{+3}$). In some embodiments, $Z^+$ is an organic species. In some embodiments, the organic species is quaternary ammonium. In some embodiments, the quaternary ammonium is a tetraalkylammonium, for example $[N(R^5)_4]^+$, wherein each $R^5$ is independently $C_{1-4}$alkyl.

In some embodiments, $R^1$ comprises a counter cation. When $R^1$ comprises a counter cation, $Z^+$ is not present. Examples of phospholipid head groups that can comprise a counter cation include any phospholipid head group comprising a basic nitrogen atom, such as choline and ethanolamine.

In some embodiments, $R^4$ is H. In some embodiments, $R^4$ is $C_{1-4}$alkyl. In some embodiments, $R^4$ is selected from methyl, ethyl, n-propyl, isopropyl, n-butyl, sec-butyl, isobutyl and tert-butyl.

In an embodiment, the compound of Formula (I) has the structure:

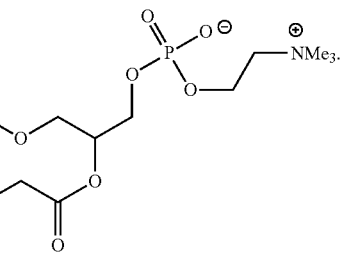

In another embodiment, the compound of Formula (I) has the structure:

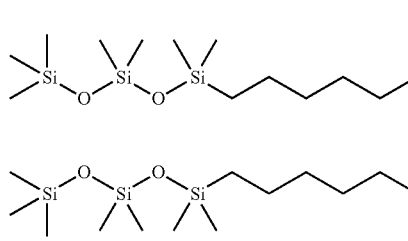

eter of about 80 nm to about 300 nm, about 90 nm to about 250 nm or about 100 nm to about 200 nm. In some embodiments, the liposomes have an average diameter of about 100 nm to about 200 nm.

In some embodiments, the liposomes have a polydispersity of about 0.1 to 0.3. In some embodiments, the liposomes have a polydispersity of about 0.1 to 0.2. The polydispersity index can be controlled by the method of manufacturing as would be known to a person skilled in the art, and determined based on the desired route of delivery.

In some embodiments, the liposomes of the application further comprise an agent. In some embodiments, the agent is encapsulated within the liposomes. In some embodiments, the agent is located in the external, outer or continuous phase of a composition comprising the liposomes. Still further, it is an embodiment that the agent is located in the bilayer structure of the liposome. In some embodiments, the agent is located in one or more of the internal phase, external phase and the bilayer structure of the liposomes.

In some embodiments, the liposomes of the application are further modified for their intended use. For example, the surface of the liposome is modified with targeting groups, such as antibodies, for directed delivery in a subject and/or the liposomes are modified with polymer groups, such as polyethylene glycol (PEG), groups to improve their ability to remain intact in, for example, the circulatory system of a subject.

Methods for the surface modification and the combination, attachment and encapsulation of agents in liposomes are known in the art.[18]

IV. Methods of Preparing Compounds

The compounds of the application can be prepared using methods known in the art. For example, in one exemplary embodiment shown in Scheme 2, a chemoenzymatic route is used wherein glycerol is reacted with two equivalents of a

III. Liposomes of the Application

The present application includes liposomes comprising one or more compounds of the application.

In some embodiments the liposomes of the application are unilamellar. In some embodiments, the liposomes are unilamellar without the need for extrusion through pre-sized membranes.

In some embodiments, the liposomes are of uniform size. In some embodiments, the liposomes have an average diamsiloxane-functionalized ester in the presence of a lipase such as Lipozyme™ followed by incorporation of the phosphate head group using standard chemistries.

Alternatively, in some embodiments, a compound of formula I(a):

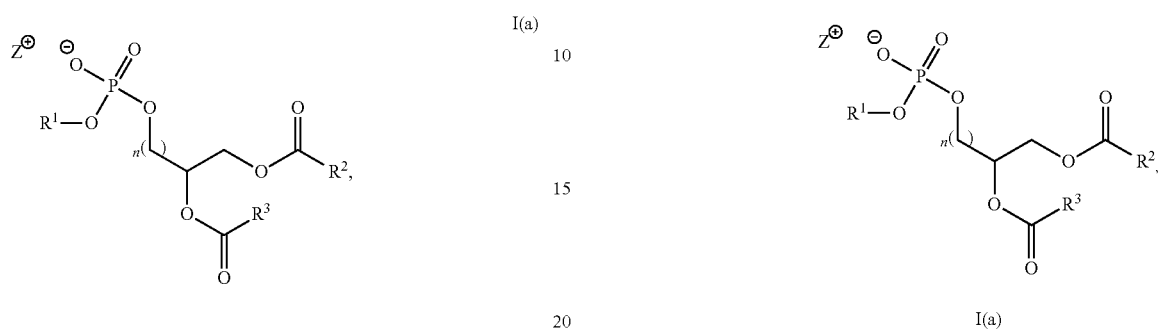

is prepared by a method comprising:

(a) reacting a compound of formula (II) with a compound of formula III(i) in the presence of a lipase catalyst under conditions to obtain a compound of formula (IV):

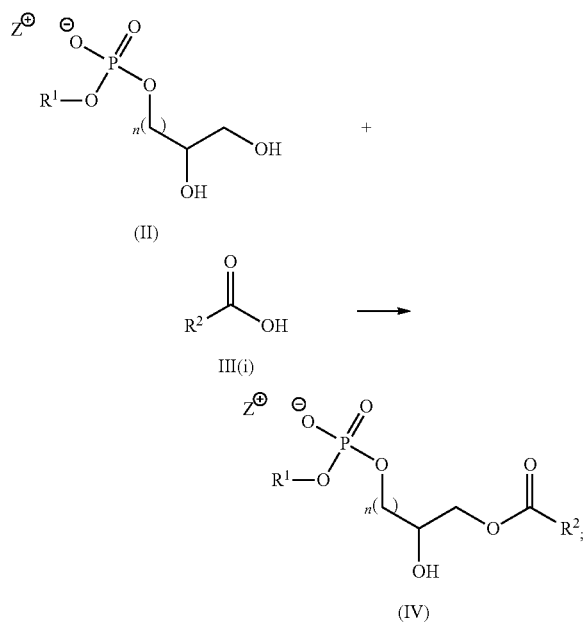

(b) reacting the compound of formula (IV) with a compound of formula III(ii) under conditions to obtain the compound of Formula I(a)

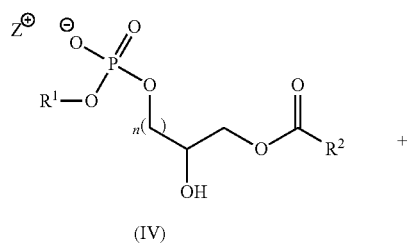

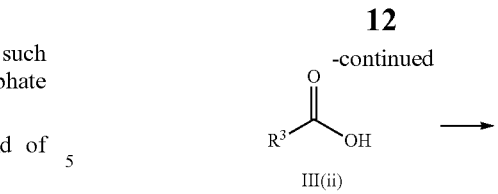

wherein in the compounds of formulae I(a), (II), III(i), III(ii) and (IV), $R^1$, $R^2$, $R^3$, n and $Z^+$ are as defined herein for the compound of Formula (I).

In an embodiment, the compound of Formula III(i) and the compound of Formula III(ii) are the same. In another embodiment, the compound of Formula III(i) and the compound of Formula III(ii) are different.

In an embodiment, the conditions for reacting the compound of Formula (II) with the compound of Formula III(i) in the presence of a lipase catalyst comprise adding the lipase catalyst to a mixture of the compound of Formula (II) and the compound of Formula III(i) and allowing the mixture to react for a time and at a temperature and pressure for the conversion of the compound of Formula (II) and the compound of Formula III(i) to the compound of Formula (IV) to proceed to a sufficient extent, for example, at a temperature of about 65° C. to about 80° C. or about 65° C. and a reduced pressure, for example a pressure of about 20 in Hg to about 40 in Hg or about 28.5 in Hg for a time of about 24 hours to about 3 days or about 48 hours. In another embodiment, the lipase catalyst is N435 (Novozyme™ 435, a lipase B from *Candida antarctica* immobilized on a macroporous acrylic resin).

In an embodiment, the conditions for reacting the compound of Formula (IV) with the compound of Formula III(ii) comprise Steglich esterification conditions. In another embodiment, the conditions comprise reacting the compound of Formula (IV) with the compound of Formula III(ii) in a suitable solvent (for example, trichloromethane) in the presence of a suitable coupling agent (for example, dicyclohexylcarbodiimide (DCC)) and catalyst (for example, 4-dimethylaminopyridine (DMAP)) and allowing the mixture to react for a time and at a temperature for the conversion of the compound of Formula (IV) and the compound of Formula III(ii) to the compound of Formula I(a) to proceed to a sufficient extent, for example, at a temperature of about 50° C. to about 70° C. or about 65° C. for a time of about 24 hours to about 72 hours or about 48 hours.

The intermediate compounds of Formula (IV) are new therefore the present application also includes a compound of Formula (IV):

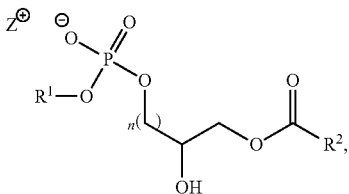

(IV)

wherein R¹, R², n and Z⁺ are as defined herein for the compounds of Formula (I).

In an embodiment, the compound of Formula (IV) has the structure:

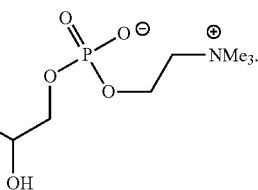

In another embodiment, the compound of Formula (IV) has the structure:

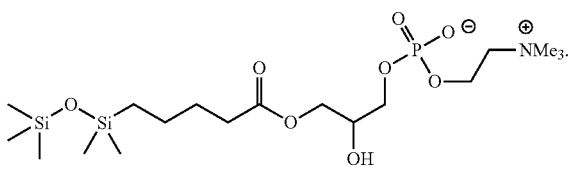

V. Compositions and Uses of the Application

The compounds of the present application are new therefore the present application includes all uses of said compounds, including uses related to medical therapies, diagnostics, and analytical tools. For example, the compounds are useful for any purpose for which other phospholipids known in the art have been employed. Therefore, the compounds of the application are useful, for example, for preparing liposomes and other 3D structures, and for modification of surfaces.[19]

In some embodiments, the compounds of the application are formed into other structures such as bicelles, ribbons and disks.

In some embodiments, as noted above, the compounds of the application are formed into liposomes to provide liposomal compositions. The liposome compositions comprising SiPCs 7 and 8 (Scheme 2) were prepared using a freeze-thaw procedure coupled with mechanical agitation, skipping extrusion through a pre-sized membrane, typically utilized to reduce the size of liposomes made with traditional lipids. This preparation technique allows the characterization of the spontaneous assembly of SiPCs in aqueous media.

Accordingly, the present application includes a method of preparing liposomes comprising subjecting an aqueous dispersion of one or more compounds of the application to one or more cycles wherein each cycle comprises freezing, thawing and mechanical agitation, to provide an aqueous suspension of liposomes comprising the one or more compounds.

In some embodiments, the freezing and thawing is performed by placing an aqueous dispersion comprising one or more compounds of the application in an environment at temperature of about −40° C. to about −10° C. for a time of about 10 min to about 2 h followed by thawing the solution at a temperature of about 20° C. to about 50° C. for a time period of about 10 min to about 2 h.

In some embodiments, after each freeze-thaw, the aqueous dispersion is subjected to mechanical agitation, for example by vortexing, for a time of about 10 s to about 60 s. An example of a suitable apparatus for vortexing is the Bio-Tec vortexer available from Bio Tec, Currumbin, Australia. Each freeze, thaw and mechanical agitation of the aqueous dispersion represents one cycle. In some embodiments, the aqueous dispersion is subjected to 1 to 10 cycles. In some embodiments, the aqueous dispersion is subjected to 1 to 8 cycles. In some embodiments, the aqueous dispersion is subjected to 1 to 6 cycles. In some embodiments, the aqueous dispersion is subjected to 5 cycles. In some embodiments, the aqueous dispersion is subjected to cycles until an opaque suspension of liposome vesicles is obtained, as determined, for example, by Small-angle X-ray Scattering (SAXS) analysis.

In some embodiments, the liposomes prepared using the method of preparing liposomes of the application are of uniform size. In some embodiments, the liposomes have an average diameter of about 80 nm to about 300 nm, about 90 nm to about 250 nm or about 100 nm to about 200 nm. In some embodiments, the liposomes have an average diameter of about 100 nm to about 200 nm. In some embodiments, the liposomes have a polydispersity of about 0.1 to 0.3. In some embodiments, the liposomes have a polydispersity of about 0.1 to 0.2.

The liposomes of the present application are new therefore the present application includes all uses of said liposomes, including uses related to medical therapies, diagnostics, and analytical tools. For example, the liposomes are useful for any purpose for which other liposomes known in the art have been employed. Therefore, the liposomes of the application are useful, for example, as drug carriers, blood cell substitutes, vaccine carriers, in protein separations, surface modifications and for biomolecule immobilizations. In these contexts, the liposomes of the present application are expected to be superior to conventional liposomes because it is easier to achieve mechanical stability, controllable size, increased loading capacity and simplified preparation on a large scale.

The present application therefore includes methods of using the liposomes of the present application, for example, for delivery of agents to a cell, tissue and/or subject. Accordingly the present application includes a method for delivering one or more agents to a biological system comprising administering liposomes of the present application to said system, wherein the liposomes comprise the active agent. Also included in the present application is a method of delivering an active agent to a subject in need of treatment with the active agent comprising administering an effective amount of liposomes of the present application to said subject, wherein the liposomes comprise the active agent.

Also included in the present application is a use of the liposomes of the present application for delivery of agents to a cell, tissue or subject as well as a use of the liposomes of the present application to prepare a medicament for delivery of agents to a cell, tissue or subject. Also included is a liposome for use to deliver agents to a cell, tissue or subject. In each of these uses, the liposome comprises the agent, suitably an active agent.

In some embodiments, the encapsulation of the active agent within the liposomes is faster than with liposomes prepared using non-siloxane containing phospholipids. Accordingly, in some embodiments, the present application includes a fast-encapsulation drug delivery system comprising the liposomes of the application. For example, in some embodiments, agents are encapsulated in liposomes of the present application in effective amounts using a single or less than 5 cycles, whereas in some prior art methods 10-25 cycles are needed.[20]

The term "effective amount" of a liposomal composition of the present application is a quantity sufficient to, when administered to the subject, including a mammal, for example a human, effect beneficial or desired results, including clinical results and diagnostic results, and, as such, an "effective amount" or synonym thereto depends upon the context in which it is being applied. For example, in the context of treating a disease, disorder or condition, it is an amount of the composition sufficient to achieve such a treatment as compared to the response obtained without administration of the composition. As a further example, in the context of diagnosing or detecting a disease, disorder or condition, it is an amount of the composition sufficient to achieve such a diagnosis as compared to the response obtained without administration of the composition. The amount of a given composition of the present application that will correspond to such an amount will vary depending upon various factors, such as the given agent in the liposomal composition, the pharmaceutical formulation, the route of administration, the type of disease, disorder or condition, the identity of the subject or host being treated, and the like, but can nevertheless be routinely determined by one skilled in the art.

Moreover, a "treatment", "prevention" or diagnostic regime of a subject with an effective amount of the composition of the present disclosure consists, for example, of a single administration, or alternatively comprises a series of applications. For example, the composition of the present application is administered at least once a week. However, in another embodiment, the composition is administered to the subject from about one time per week to about once daily for a given treatment. The length of the treatment period depends on a variety of factors, such as the severity of the disease or disorder, the age of the patient, the concentration and the activity of the active agents in the composition of the present disclosure, or a combination thereof. It will also be appreciated that the effective dosage of the composition used for the treatment or prophylaxis is optionally increased or decreased over the course of a particular treatment or prophylaxis regime. Changes in dosage result and become apparent by standard diagnostic assays known in the art. In some instances, chronic administration is required. It will also be appreciated that, for diagnostic applications, the compositions of the disclosure are only administered once, for example, prior to the diagnostic assay.

As used herein, and as well understood in the art, "treatment" is an approach for obtaining beneficial or desired results, including clinical results. Beneficial or desired clinical results include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" also means, for example, prolonging survival as compared to expected survival if not receiving treatment.

The present disclosure further includes a pharmaceutical composition comprising the liposomes of the application and a pharmaceutically acceptable carrier. In an embodiment, the liposomes comprise an agent, suitably an active agent.

The present application also includes a use of the liposomes of the application as medicaments.

In some embodiments of the application, the compositions of the application are introduced or incorporated into medical devices for delivery to a specific treatment site, or for controlled release. Alternative uses of the compositions of the application include, but are not limited to: cell replacement therapies, for example, red blood cell replacement; stabilizers for protein and peptide-based drugs and therapeutics, for example by stabilizing such compounds to reduce aggregation and/or precipitation of these macromolecules; vaccine carriers, for example to improve the shelf life of peptides vaccines; immunologic adjuvants, for example to activate phagocytosis by macrophages; cell conjugation; gene therapy; gene transfection; or in diagnostic disclosures.

VI. Formulations and Dosing

The liposomes of the application can be administered per se or as a pharmaceutical composition or formulation. Accordingly, the present application also includes pharmaceutical compositions comprising agents encapsulated in the liposomes of the application admixed with at least one pharmaceutically acceptable carrier. In some embodiments, the pharmaceutical composition provides sustained release of agents and therefore comprises a sustained release formulation.

The liposomes or pharmaceutical compositions or formulation thereof are administered to a subject using any suitable route, for example, intravenous administration, intraarterial administration, intramuscular administration, intraperitoneal administration, subcutaneous administration, intradermal administration, transdermal administration, epicutaneous administration, intraarticular administration, intrathecal administration, intracerebroventricular administration, as a nasal spray, via pulmonary inhalation, and oral administration, as well as other suitable routes of administration known to those skilled in the art, and are formulated accordingly.

Depending on the mode of administration, pharmaceutical compositions may be in the form of liquid, solid, or semi-solid dosage preparations. For example, the compositions may be formulated as solutions, dispersions, suspensions, emulsions, mixtures, lotions, liniments, jellies, ointments, creams, pastes (including toothpastes), gels, hydrogels, aerosols, sprays (including mouth sprays), powders (including tooth powders), granules, granulates, lozenges, salves, chewing gum, pastilles, sachets, mouthwashes, tablets, dental floss, plasters, bandages, sheets, foams, films, sponges, dressings, drenches, bioadsorbable patches, sticks, tablets, buccal tablets, troches, capsules, elixirs, suspensions, syrups, wafers, modified release tablets, and the like.

The pharmaceutical compositions of the present application may be formulated according to general pharmaceutical practice (see, for example, Remington's Pharmaceutical Sciences (2000-20th edition) and in The United States Pharmacopeia: The National Formulary (USP 34 NF19)).

Pharmaceutically acceptable carriers for use with the pharmaceutical compositions of the application can be routinely selected for a particular use by those skilled in the art. These include, but are not limited to, solvents, buffering agents, inert diluents or fillers, suspending agents, dispersing or wetting agents, preservatives, stabilizers, chelating agents, emulsifying agents, anti-foaming agents, gel-forming agents, ointment bases, penetration enhancers, humectants, emollients, and skin protecting agents.

Examples of solvents are water, alcohols, vegetable, marine and mineral oils, polyethylene glycols, propylene glycols, glycerol, and liquid polyalkylsiloxanes. Inert diluents or fillers may be sucrose, sorbitol, sugar, mannitol, microcrystalline cellulose, starches, calcium carbonate, sodium chloride, lactose, calcium phosphate, calcium sulfate, or sodium phosphate. Examples of buffering agents include citric acid, acetic acid, lactic acid, hydrogenophosphoric acid, and diethylamine. Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans. Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a pharmaceutical composition of the application to prevent microbial contamination that can affect the stability of the formulation and cause infection in the patient. Suitable examples of preservatives include parabens (such as methyl, ethyl, propyl, p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol. Examples of chelating agents include sodium EDTA and citric acid.

Examples of emulsifying agents are naturally occurring gums, naturally occurring phosphatides (e.g., soybean lecithin; sorbitan mono-oleate derivatives), sorbitan esters, monoglycerides, fatty alcohols, and fatty acid esters (e.g., triglycerides of fatty acids). Anti-foaming agents usually facilitate manufacture, they dissipate foam by destabilizing the air-liquid interface and allow liquid to drain away from air pockets. Examples of anti-foaming agents include simethicone, dimethicone, ethanol, and ether.

Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carrageenans, hyaluronates, and alginates. Ointment bases suitable for use in the compositions of the present application may be hydrophobic or hydrophilic, and include paraffin, lanolin, liquid polyalkylsiloxanes, cetanol, cetyl palmitate, vegetable oils, sorbitan esters of fatty acids, polyethylene glycols, and condensation products between sorbitan esters of fatty acids, ethylene oxide (e.g., polyoxyethylene sorbitan monooleate), and polysorbates.

Examples of humectants are ethanol, isopropanol glycerin, propylene glycol, sorbitol, lactic acid, and urea. Suitable emollients include cholesterol and glycerol. Examples of skin protectants include vitamin E, allatoin, glycerin, zinc oxide, vitamins, and sunscreen agents.

In some embodiments, the liposomal compositions of the present application are lyophilized or freeze-dried. Techniques for liposome lyophilization are well known, for example, Chen et al. (J. Control Release 2010 Mar. 19; 142(3):299-311) summarizes key factors determining the lyoprotective effect of freeze-dried liposomes.

The compositions of the application will generally be used in an amount effective to achieve the intended result, for example in an amount effective to treat or prevent the particular condition, disease or disorder being treated. The dose and/or ratio of an agent administered to the subject using the compositions of the application are readily determined by those of skill in the art.

In some embodiments, the compositions, or formulations thereof, of the application are administered intravenously over an extended time period, for example over about 1 minute to several hours, for example, 2, 3, 4, 6, 24 or more hours.

In some embodiments, the treatment is administered once a day. In some embodiments, the treatment is administered twice a day. In some embodiments, the treatment is administered three times a day. In some embodiments, the treatment is administered four times a day. In some embodiments, the treatment is administered one to two times a day for one, two, three, four, five, six or seven days. In some embodiments, the treatment is administered at least once a day for a longer term such as 1, 2, 3, 4, 5, 6, 7, 8, 9, 10, 11 or 12 weeks. In some embodiments, the treatment is administered at least once a day until the condition has ameliorated to where further treatment is not necessary. In some embodiments, the treatment provides sustained release of the agent and administration is require less frequently, for example, once a week, once a month, once every 6 months, once every year, once every two years, or once every five years.

In some embodiments, the treatment is administered at least once per week. In some embodiments, the treatment is administered twice per week. In some embodiments, the treatment is administered three times per week. In some embodiments, the treatment is administered four times per week. In some embodiments, the treatment is administered five times per week. In some embodiments, the treatment is administered six times per week. In some embodiments, the treatment is administered one to six times per week for one, two, three, four, five, six or seven weeks. In some embodiments, the treatment is administered at least once per week for a longer term such as 1, 2, 3, 4, 5, 6, 7, 8, 9, 10, 11 or 12 weeks. In some embodiments, the treatment is administered at least once per week until the condition has ameliorated to where further treatment is not necessary.

In some embodiments, the treatment may be administered as a continuous, intermittent or patient-controlled infusion using an infusion pump. In some embodiments an infusion pump is used to administer the treatment intravenously.

The following non-limiting examples are illustrative of the present application:

EXAMPLES

Example 1: Synthesis of Trisiloxane Phosphocholines

I. Synthetic Procedures 2-hydroxypropane-1,3-diyl bis(10-(1,1,3,3,5,5,5-heptamethyltrisiloxanyl)decanoate)

A round bottomed flask was charged with glycerol (81.2 mg, 0.88 mmol) and the trisiloxane methyl ester (582.0 mg, 1.81 mmol). To this mixture was added 63.0 mg Lipozyme™ (10 wt % with respect to the mass of the monomers) and the mixture was stirred at 50° C. for 72 h. The reaction mixture was cooled to room temperature and diluted with 10 mL of chloroform. The beads were filtered from the reaction mixture using a medium porosity Büchner funnel and solvent was evaporated in vacuo. The crude residue was purified by column chromatography on silica gel using 9:1 hexanes:ethyl acetate to give 37.7 mg (0.056 mmol, 7%) of 3 and 101.5 mg (0.151 mmol, 18%) of 4 as clear and colourless oils. 4: $^1$H NMR (300 MHz, CDCl$_3$): δ 0.02 (s, 12H), 0.06 (s, 12H), 0.08 (s, 12H), 0.52 (m, 4H), 1.28 (br, 24H), 1.63 (m, 4H), 2.35 (t, J=7.5 Hz, 4H), 2.41 (d, J=4.5 Hz), 4.14 (m, 5H); $^{13}$C NMR (75 MHz, CDCl$_3$, TMS at 0.0 ppm): δ 0.2, 1.3, 1.8, 18.3, 23.2, 24.9, 29.1, 29.29, 29.32, 29.4, 33.4, 34.1, 65.0, 68.4, 173.9; $^{29}$Si NMR (59.6 MHz, CDCl$_3$): δ −21.1, 7.0, 7.4; ATR-IR (2 cm$^{-1}$): 1042, 1254, 1741, 2853, 2922, 2956, 3460; ESI$^+$ MS (m/z): (M+Na)$^+$=863.6.

1,2-SiPC (7)

To a stirred solution of 95.3 mg (0.11 mmol) of 3 in 4 mL of toluene were added 0.13 mmol of triethylamine and the mixture was cooled on an ice bath. 2-chloro-1,3,2-dioxaphospholane-2-oxide (0.128 mmol) was dissolved into toluene and added to 3 in a single aliquot and stirred while warming to room temperature over 18 h. Triethylammonium hydrochloride salts were removed by filtration and the solvent was removed in vacuo to yield a viscous liquid which was phosphate positive by $^{31}$P NMR. This product was not characterized further but instead was dissolved into 5 mL of acetonitrile, transferred to a pressure resistant reaction vessel, and cooled to −30° C. in an acetone/liquid nitrogen bath. Trimethylamine was bubbled into the reaction mixture for 1.5 h after which time the contents of the reaction were heated to 65° C. for 24 h. 1,2-SiPC was purified by column chromatography on silica gel (200-400 mesh) using an isocratic elution solvent of 65:25:4 CHCl$_3$:MeOH:H$_2$O to give 10.2 mg (1.04×10$^{-5}$ mmol) of an opaque gel. Spectroscopy: $^1$H NMR (300 MHz, CDCl$_3$): δ 0.01 (s, 6H), 0.5 (s, 6H), 0.8 (s, 9H), 0.52, (m, 4H), 1.26 (br, 24H), 1.57 (m, 4H), 2.26 (t, 2H), 2.29 (t, 2H), 3.36 (s, 9H), 3.81 (br, 2H), 3.95 (br, 2H), 4.11 (m, 1H), 4.37 (br, 3H), 5.20 (br, 1H); $^{13}$C NMR (75 MHz, CDCl$_3$): δ 0.2, 1.3, 1.81, 18.3, 23.3, 24.9, 25.0, 29.2, 29.4, 29.5, 33.5, 34.1, 34.3, 54.5, 63.0, 173.3, 173.6; $^{29}$Si NMR (59.6 MHz, CDCl$_3$): δ −21.0, 7.0, 7.4; $^{31}$P NMR (121 MHz, CDCl$^3$): δ −0.84; ATR-IR (CHCl$_3$, 2 cm$^{-1}$): 969, 1044, 1254, 1736, 2852, 2921, 2956; ESI$^+$ MS (m/z): [M+Na]$^+$ 1028.5.

1,3-SiPC (8)

To a stirred solution of 348.6 mg (0.42 mmol) of 4 in 10 mL of diethyl ether were added 0.51 mmol of triethylamine and the mixture was cooled on an ice bath. 2-chloro-1,3,2-dioxaphospholane-2-oxide (0.5 mmol) was dissolved into toluene and added to 4 in a single aliquot and stirred while warming to room temperature over 18 h. Triethylammonium hydrochloride salts were removed by filtration and the solvent was removed in vacuo to yield a viscous liquid which was phosphate positive by $^{31}$P NMR. This product was not characterized further but instead was dissolved into 10 mL of acetonitrile, transferred to a pressure resistant reaction vessel, and cooled to −30° C. in an acetone/liquid nitrogen bath. Trimethylamine was bubbled into the reaction mixture for 1.5 h after which time the contents of the reaction were heated to 60° C. for 24 h. 1,2-SiPC was purified by column chromatography on silica gel (200-400 mesh) using an isocratic elution solvent of 65:25:4 CHCl$_3$:MeOH:H$_2$O to give 36.8 mg (3.7×10$^{-5}$ mmol) of an opaque gel. Spectroscopy: 1H NMR (300 MHz, CDCl$_3$): δ 0.01 (s, 6H), 0.05 (s, 6H), 0.78 (s, 9H), 0.52 (m, 4H), 1.26 (br, 24H), 1.75 (m, 4H), 2.30 (t, J=7.5 Hz, 4H), 3.39 (s, 9H), 3.90 (br, 2H), 4.23 (br, 4H), 4.37 (br, 2H), 4.49 (br, 1H); $^{13}$C NMR (75 MHz, CDCl$_3$): δ 0.2, 1.3, 1.8, 18.3, 23.3, 24.9, 29.2, 29.4, 29.5, 33.5, 34.1, 54.4, 59.5, 62.9, 66.54, 70.4, 173.5; $^{29}$Si NMR (59.6 MHz, CDCl$_3$): δ −21.1, 7.0, 7.4; $^{31}$P NMR (121 MHz, CDCl$^3$): δ −1.39; ATR-IR (CHCl$_3$, 2 cm$^{-1}$): 1045, 1215, 1254, 1732, 2854, 2923, 2957, 3018; ESI$^+$ MS (m/z): [M+Na]$^+$ 1028.5.

II. Instrumentation

Nuclear magnetic resonance spectroscopy ($^1$H, $^{13}$C{$^1$H}, $^{29}$Si{$^1$H}, $^{31}$P{$^1$H}) was performed using a Bruker Avance AV-300 spectrometer using CDCl$_3$ as solvent. Electrospray Ionization mass spectrometry (ESI$^+$) was carried out on a Bruker HCT Ultra instrument while high resolution Fast Atom Bombardment mass spectrometry (FAB$^+$) was carried out on a Thermo DFS instrument. ATR-IR spectra were acquired on a Bruker Alpha Optic GmBH spectrometer and analyzed using OPUS 7.2 software.

III. Results and Discussion

The present studies investigated synthesizing silicon-containing phospholipids with the goal of designing lipid nanoparticle delivery vehicles. The hydrophobic nature of siloxanes may, for example, compliment the hydrophobic nature of the fatty acid tails of phospholipids.

Herein is reported the first generation synthesis of two new silicon-containing phosphocholines (SiPCs) in which the fatty acid chains are terminated by trisiloxane units. Immobilized lipases can, for example, be used in the field of organosilicon chemistry and the present example uses such a biocatalytic approach. Heptamethyltrisiloxane-modified decanoic acid esters were used as the starting point for the chemo-enzymatic synthesis of SiPCs.[21]

The synthetic strategy relied on successive chemo-enzymatic esterifications between anhydrous glycerol (2) and 1-(methyl-9-carboxynonyl)-1,1,3,3,5,5,5-heptamethyltrisiloxane methyl ester (1).[22] Two equivalents of the methyl ester (1) were combined with glycerol (2) in the presence of Lipozyme™ (an immobilized lipase from *Rhizomucor miehei*) for 72 h to give a mixture of acyl glycerides (3) and (4), Scheme 2.

Scheme 2: Synthetic strategy employed in the synthesis of siloxane phospholipids.

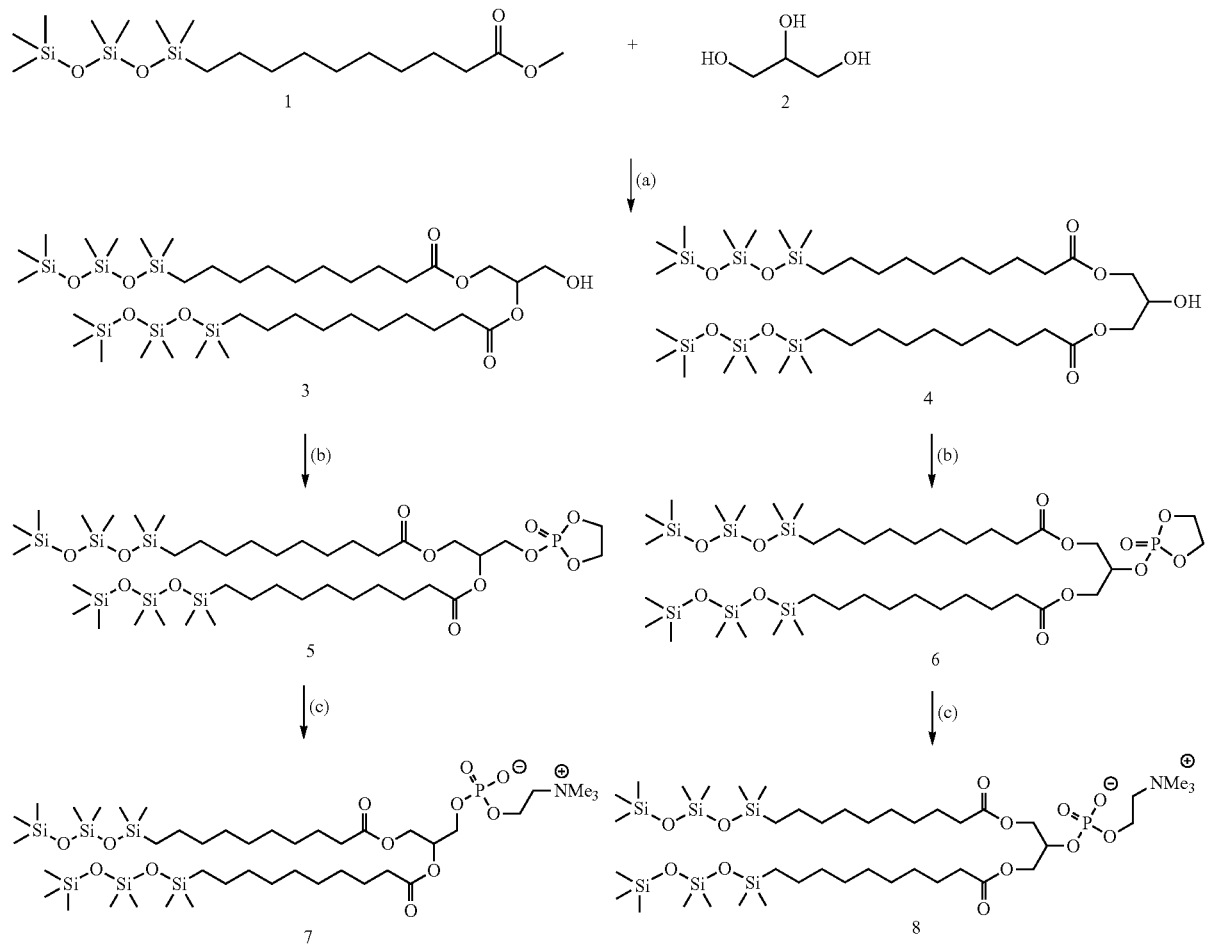

(a) 10 wt % Lipozyme RM, 40° C., 72 h; (b) 2-chloro-1,3,2-dioxaphospholane-2-oxide, NEt₃, PhH; (c) NMe₃, AcCN, -40° C. to RT.

Even though Lipozyme is known to have sn-1,3 selectivity,[23] which would normally favour the synthesis of 1,3-diacylglycerides (1,3-DAG), 1,2-diacyl glyceride (1,2-DAG) and triacylglyceride (TAG) were also found to result from the reaction. Rearrangement of glycerol esters typically proceeds via acyl migration from either of the primary hydroxyl groups to the secondary alcohol. Acyl migration was found to occur upon sitting at room temperature, or in a −20° C. freezer, and small amounts of the other isomer and TAG were detected by $^1$H NMR. Using two to four excess equivalents of ester has been proposed as a method to eliminate acyl migration.[24] However, with the products of the present substrates, column chromatography needed to be performed three or four times and, as such, this method was not employed. After column chromatography on the crude reaction mixture, diacylglycerides (3) and (4) were isolated in 10% and 21% yield, respectively.

New compound 1,2-SiPC (7) was synthesized by first adding 2-chloro-1,3,2-dioxaphospholane-2-oxide to a solution of (3) in benzene to afford intermediate (5) under reaction conditions previously reported.[25] The insoluble NEt₃.HCl salts were removed by filtration and the remaining solvent was evaporated to give a slightly opaque viscous oil that was phosphate positive showing a single $^{31}$P NMR resonance at 17.3 ppm. As per previous reports, compound (5) was not characterized further but was used in the reaction as soon as possible to avoid hydrolysis of the dioxaphospholane ring. The crude residue was dissolved into acetonitrile, cooled to −30° C. and gaseous trimethylamine (liberated from NMe₃.HCl with concentrated NaOH solution) was bubbled into the reaction over 1.5 hours after which time the reaction mixture was sealed and heated to 65° C. for 24 hours. 1,2-SiPC (1) was isolated in 9.2% yield as a waxy solid. The $^1$H NMR spectrum showed the characteristic trimethylammonium resonance of choline at 3.45 ppm and three singlets between 0.01-0.08 ppm for the trisiloxane unit which remained unaltered during the course of the reaction. $^{31}$P NMR showed a single resonance at −0.84 ppm which agreed well with other phosphocholines.

The same procedure was employed for the synthesis 1,3-SiPC (8). After two steps, (8) was isolated in 8.8% yield. The $^1$H NMR spectrum showed the characteristic resonances for the trimethylammonium and trisiloxane groups; the $^{31}$P NMR resonance was found at −1.39 ppm showing only a minor difference from (4).

The interfacial phase behaviour of lipids and phospholipids is an important area of study. Data from Langmuir isotherms can give insight into packing behaviour and collapse mechanisms of phospholipid monolayers. FIG. 1 presents the Langmuir isotherms for 1,2-SiPC, 1,3-SiPC, 1,2-dipalmitoyl-sn-3-phosphocholine (DPPC), and 1-palmitoyl-2-oleoyl-sn-3-phosphocholine (POPC). DPPC and POPC are biologically relevant lipids that are commonly used as model systems in the study of membrane topology. These two lipids differ in the degree of unsaturation with POPC containing a single unit of unsaturation in the oleic acid FA chain. Inspection of the isotherms of the SiPCs suggests that the interfacial behaviour of the monolayers resembles more closely that of POPC rather than DPPC in that the increase in surface pressure increases smoothly until monolayer collapse which occurs between 47-50 mN/m. The surface area at the collapse of 1,2-SiPC was approximately 70 Å$^2$ and that for 1,3-SiPC was 87 Å$^2$. Both of these values are larger than those observed for DPPC and POPC.

While not wishing to be bound by theory, the larger size of the siloxane tails strongly affects the mean molecular area of the lipid as well as the lipid area at monolayer collapse. Furthermore, the rotational freedom of the siloxane unit leads to behaviour similar to that for unsaturated phospholipids such as POPC. Unlike DPPC monolayers which exhibit a coexistence of liquid expanded and liquid condensed phases, Langmuir isotherms of the SiPCs are devoid of any obvious phase coexistence.

Presented herein is the first known synthesis of phospholipids bearing siloxane groups. These hybrid lipids may, for example, have interesting biophysical properties which makes them useful in medicine as delivery vehicles.

Example 2: Synthesis and Bilayer Properties of Trisiloxane Phosphocholines

I. Methods and Materials

SiPC Aqueous Dispersions.

SiPCs were prepared as described above in Example 1. Aqueous dispersions of SiPCs were prepared by five freeze-thaw cycles to give opaque suspensions of vesicles suitable for Small-angle X-ray scattering (SAXS) analysis. Dispersion particle size was determined by dynamic light scattering (DLS) with a Nano Zetasizer ZS90 (Malvern Instruments, Worcestershire, U.K.).

Preparation of Unilamellar Vesicles (ULVs):

1-Palmitoyl-2-oleoyl-sn-3-glycercophosphocholine (POPC) and 1-palmitoyl-2-oleoyl-sn-3-glcyercophosphoglycerol (POPG) were purchased from Avanti Polar Lipids (Alabaster, Ala.) and used as received. POPC and 5 mol % POPG were co-dissolved in a chloroform:methanol (3:1) mixture. POPC was doped with 5 mol % POPG, to minimize pauci-lamellar vesicle contamination. Solvent was removed under a gentle stream of dry nitrogen gas then was put under vacuum for 8 hours. POPC:POPG film was hydrated with ultrapure water to a concentration of ~30 mg/mL. ULVs were prepared using a manual miniextruder (Avanti Polar Lipids, Alabaster, Ala.), assembled with a 100 nm pore-diameter polycarbonate filter. The lipid suspension was passed through the filter 31 times. SAXS data were collected at the P12 BioSAXS beamline at the storage ring PETRA III (synchrotron DESY, Hamburg)[26] at a temperature of 20° C. SAXS data were visualized, averaged and the background was subtracted using ATSAS[27] and modelled using the method of Pabst et al.[28] The data was fit utilizing a standard non-linear least-squares fitting (NLSF) scheme within Origin (OriginLab, USA). Vesicle size was determined by dynamic light scattering (DLS) with a Nano Zetasizer ZS90 (Malvern Instruments, Worcestershire, U.K.)

Figure 2:
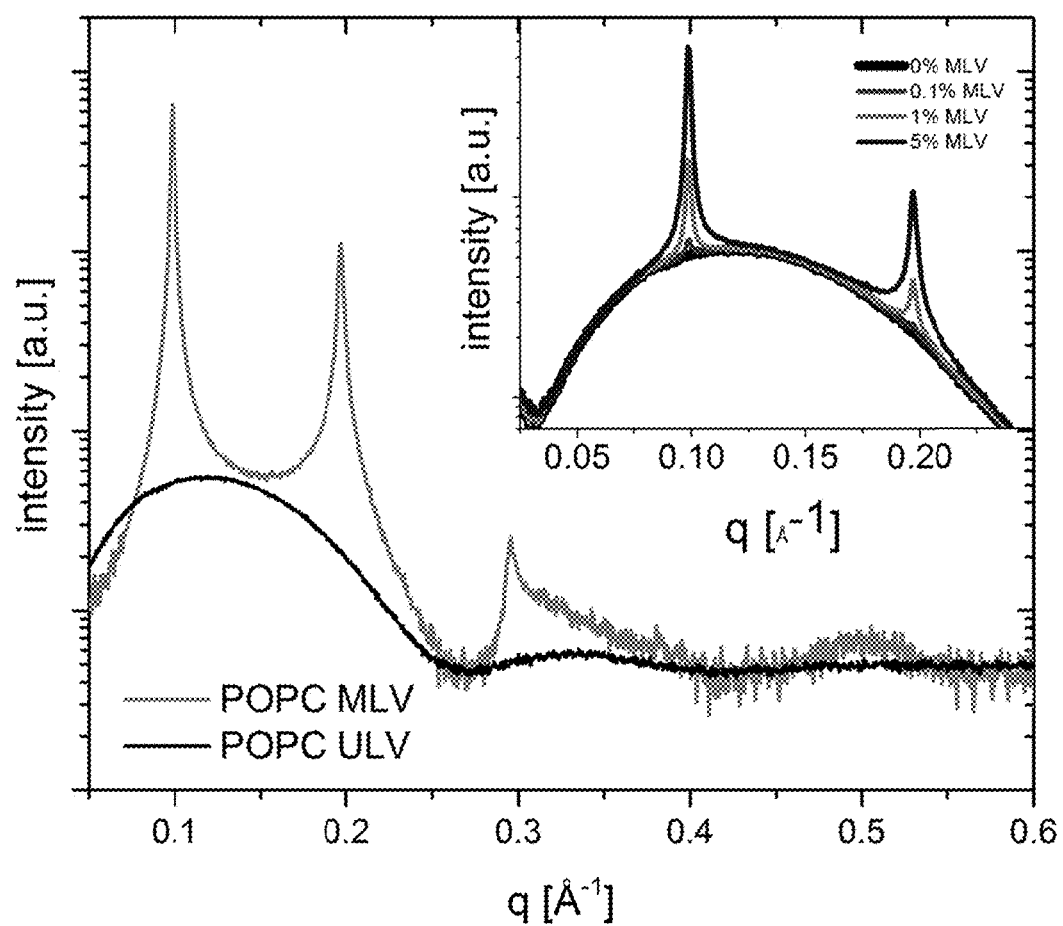
FIG. 2 is a plot of intensity as a function of q, showing the small-angle X-ray scattering (SAXS) sensitivity to multilamellar vesicles (MLVs).

SAXS is sensitive to the presence of multilamellar vesicles (MLVs) and is used to evaluate the presence of MLVs. Shown in FIG. 2 are SAXS data for an about 40 mM POPC vesicle suspension in water as 100 nm ULV (black) and MLVs (gray). For MLVs, density correlations between the stacked bilayers give rise to a bilayer-bilayer structure factor also known as Bragg Peaks at a length scale corresponding to integer multiples of the lamellar repeat distance (e.g., the first Bragg order at q~0.1 Å$^{-1}$, corresponding to a lamellar repeat distance of ~63 Å). In the ULV sample, Bragg peaks are not observed, and vesicles exhibit the typical diffuse scattering for a spherical shell particle. The inset shows a weighted sum of the black and gray curves as indicated in the inset legend, demonstrating the sensitivity of SAXS to the presence of MLVs.

3-Gaussian SAXS Model:

The scattering regime where bilayer structure (as opposed to vesicle sphericity) dominates the form factor is of most interest as information about vesicle size is obtained from the DLS. The scattered intensity of a dilute vesicle suspension is given by:

$$I(q) \propto \frac{S(q)|F(q)|^2}{q^2} \qquad (1)$$

where S(q) is the inter-particle structure factor (equal to unity in the infinite dilution limit), F(q) is the form factor. F(q) contains information about the distribution of matter in the bilayer, more specifically it characterizes the electron density distribution. Mathematically F(q) is the Fourier Transform of the electron density distribution.

The functional model chosen to describe the electron density of the siloxane phospholipids is the three Gaussian model as outlined by Pabst et al. (2000).[28] In this model, the electron distribution is the summation of the headgroups, described by a single Gaussian (in total 2, one for each leaflet of the bilayer) and a Gaussian representing the hydrocarbon chains, Eqn 2.

$$\rho(z) = [\rho_H - \rho_w] \qquad (2)$$
$$\left(\exp\left(-\frac{(z-z_H)^2}{2\sigma_H}\right) + \exp\left(-\frac{(z+z_H)^2}{2\sigma_H}\right)\right) + [\rho_C - \rho_w]\left(\exp\left(-\frac{(z)^2}{2\sigma_C}\right)\right)$$

The position of the Gaussian peak is at $z_i$ where i=H or C and $z_C$=0, with a standard deviation of $\sigma_i$. For simplicity, $\rho_H-\rho_w$ and $\rho_C-\rho_w$ are referred to herein as $\overline{\rho_H}$ and $\overline{\rho_C}$ respectively. The form factor of this electron density model can then be calculated analytically by applying Eqn 3:

$$F(q) = \int \rho(z)\exp(iqz)dz \qquad (3)$$

which yields:

$$F(q) = 2\sqrt{2\pi}\,\sigma_H \qquad (4)$$
$$\overline{\rho_H}\left(\exp\left(-\frac{(\sigma_H q)^2}{2}\right)\right)\cos(qz_H) + \sqrt{2\pi}\,\sigma_C\overline{\rho_C}\left(\exp\left(-\frac{(\sigma_C q)^2}{2}\right)\right)\cos(qz_C)$$

Only the cosine terms remain due to the centrosymmetric nature of a single component lipid bilayer. A benefit of this method is that structural parameters can be derived from simple geometric relationships, without the need of volumetric data. Typically area per lipid $A_L$ is one of the more desirable structural parameters to be extracted from the data. To begin, the transverse structure of the bilayer is derived (along the bilayer normal), such as the hydrocarbon length ($d_C$) and the headgroup thickness ($d_H$). Simply, dH can be estimated from the full width at half maximum (FWHM) of the Gaussian describing the headgroups. Using $d_H$, $d_C$ can be determined as:

$$d_C = z_H - \frac{d_H}{2} \quad (5)$$

Furthermore, the bilayer thickness ($d_B$) is:

$$d_B = z_H + \frac{d_H}{2} \quad (5)$$

Equipped with the transverse structural parameters, the higher dimensional parameters such as $A_L$ and $V_C$ can be obtained. $A_L$ is:

$$A_L = \frac{1}{\rho_W(\rho_H/\rho_C)}\left(\frac{\rho_H/\rho_C n_C^e}{d_C} - \frac{n_H^e}{d_H}\right) \quad (6)$$

where $n^e_c$ is the number of hydrocarbon electrons and $n^e_H$ the number of headgroup electrons, respectively.

Finally, the volume of the lipid can be calculated by:

$$V_L = A_L \frac{d_B}{2} \quad (7)$$

Because the volume of the PC headgroup is well characterized and known to be invariant to the phase and temperature[29] of the lipid hydrocarbon volume ($V_C$) can be determined by subtracting 331 Å$^3$.

Figure 3:
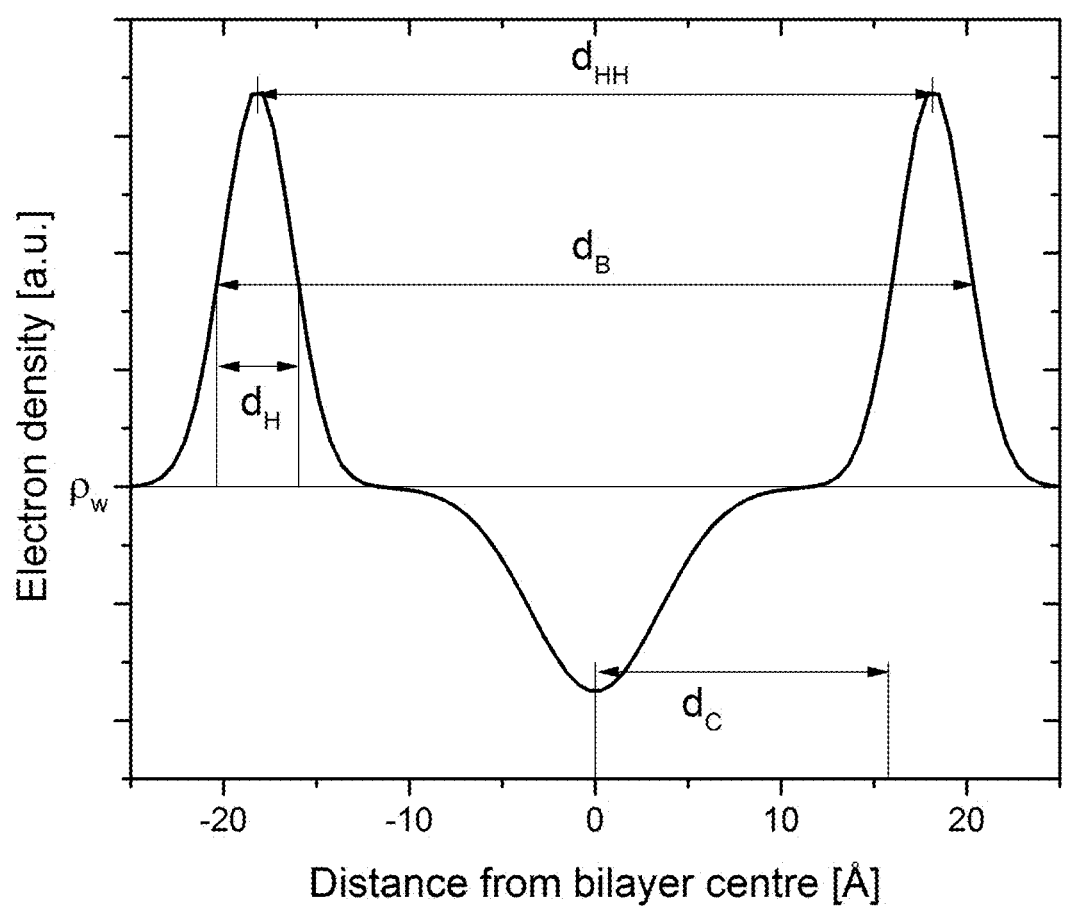
FIG. 3 is a plot of electron density profile model p(z) as a function of distance from the bilayer centre (z).

FIG. 3 shows the electron density profile model $\rho(z)$ as a function of distance from the bilayer centre (z). Key transverse structural parameters ($d_H$, $d_{HH}$, $d_B$ and $d_C$) are represented.

II. Results and Discussion

The two siloxane-containing phosphocholines (SiPCs) were prepared as described in Example 1. Liposomal preparations of SiPCs (7) and (8) were prepared using a freeze-thaw procedure, skipping extrusion through a pre-sized membrane, in order to characterize their spontaneous assembly in aqueous media. Liposomes were characterized by dynamic light scattering (DLS) and SAXS and compared to the prototypical phospholipid, 1-palmitoyl-2-oleoyl-sn-3-glycerophosphocholine (POPC) doped with 5 mol % of the anionic lipid palmitoyl-2-oleoyl-sn-3-glycerophosphocglycerol (POPG).

SiPCs were synthesized to include a fatty acid chains that contained 16 atoms so that a comparison could be made with physiologically relevant model lipid systems which typically possess fatty acid chains of 16-22 atoms.

Figure 4:
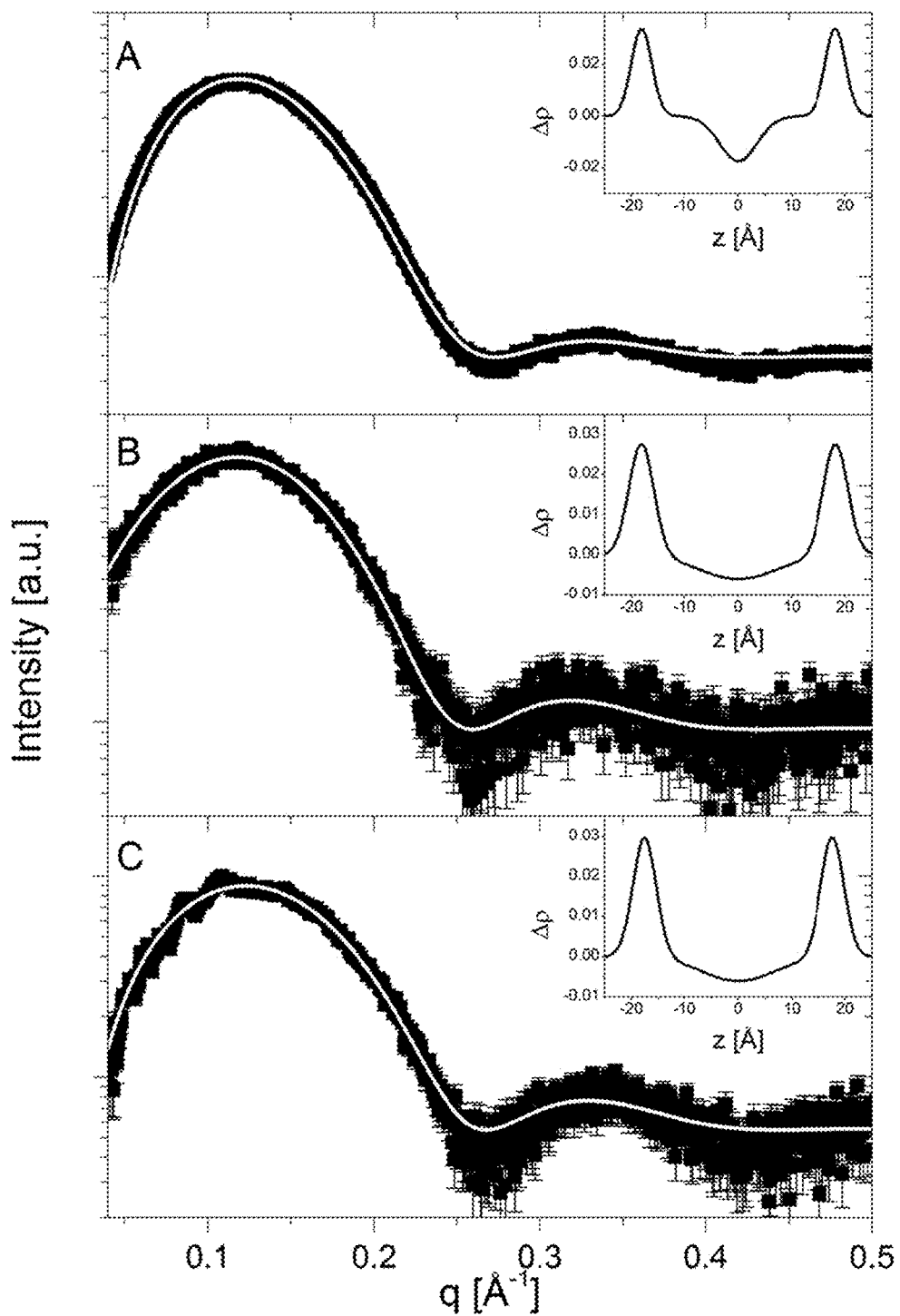
FIG. 4 shows SAXS data for unilamellar vesicles (ULVs) of (A) 1-palmitoyl-2-oleoyl-sn-3-glycercophosphocholine (POPC), (B) 1,2-SiPC, and (C) 1,3-SiPC, in exemplary and comparative embodiments of the present application. The insets show the electron density profiles as a function of distance from the centre of the bilayer.

SAXS data were taken at the EMBL-BioSAXS beamline at DESY (Hamburg, Germany) using 20 keV photons. SAXS data were visualized, averaged and the background was subtracted using data analysis software ATSAS 2.7.1.[30] Qualitative inspection of the SAXS curves for 1,2-SiPC and 1,3-SiPC (FIG. 4) revealed a characteristic bilayer form factor without the presence of a bilayer-bilayer structure factor (Bragg Peak). The characteristic signature of a structure factor is demonstrated in FIG. 2.

The spontaneous formation of a unilamellar moiety is in contrast to most phosphocholine phospholipids which exhibit attractive inter-bilayer forces yielding spontaneous formation of MLVs (FIG. 2). The lack of structure factor in the SiPC data allowed for the electron density distribution to be modelled using the method of Pabst et al.[31] In short, the modelled electron density distribution is the summation of the head groups, described by a single Gaussian (in total 2, one for each leaflet of the bilayer) and a Gaussian representing the hydrophobic core. A detailed description of the model is included in the materials and methods section, hereinabove. The advantage of this method is that structural parameters can be derived from simple geometric relationships, without the need for secondary volumetric data. To reduce the parameter dependency of the fitting procedure the volume of the PC head group was assumed to be constant, holding the parameter fixed at 331 Å$^3$ as previously determined by Kučerka and co-workers.[34] The validity of this assumption is demonstrated by the phosphocholine (PC) head group volume remaining constant irrespective of the temperature, lipid phase or chain composition.[32,33] The experimental and modelled SAXS curves for POPC are presented in FIG. 4A.

Although this model has previously been validated using both Bragg and diffuse scattering,[15] the model and instrument quality were checked using only the diffuse scattering of the prototypical phospholipid POPC. The optimized POPC fit parameters from our analysis, Table 1, are in excellent agreement with the values determined by Pabst et al.[28] Furthermore, the geometrically derived parameters (Table 1) are in agreement with the high resolution structural Scattering Density Profile (SDP) model determination of Kučerka et al.[34] For example, the hydrocarbon length ($d_C$), the headgroup-headgroup distance ($d_{HH}$) and the bilayer thickness ($d_B$) of POPC were determined to be 14.4 Å, 36.3 Å, and 43.7 Å respectively. For the same parameters, $d_C$, $d_{HH}$, and $d_B$, the SDP analysis yielded 14.6 Å, 37.4 Å, and 39.8 Å.[34] Interestingly, the derived $A_L$ (58.9±2 Å) is in reasonable agreement with the SDP model derived (62.7±1 Å) and the geometrically determined hydrocarbon volume is within 5% of the experimentally measured volume for PO chains.[27]

Fit parameters and the geometrically derived structural parameters for SiPCs are summarized in Table 1. The 3-Gaussian model allows for a reasonable estimate of the volume of the hydrocarbon chains to be determined without secondary measurements. Volumetric measurements using conventional densitometry protocols were not possible given the limited quantity of SiPC lipid produced.[35] The derived lipid volume of 1,2-SiPC and 1,3-SiPC were 1574 Å$^3$ and 1577 Å$^3$ respectively, a factor of 7 larger than the volume from the atomic covalent radii. The large volume determined for the SiPCs implies significant disorder in the bilayer core and is very comparable with the volume determined for 1,2-diphytanoyl-sn-glycero-3-phosphatidylcholine (diPhyPC).[27] However, the derived $A_L$ are lower for the SiPC than diPhyPC (78 Å$^2$) and are more in line with the $A_L$ of a polyunsaturated fatty acid-containing phosphocholines.[36]

Figure 5:
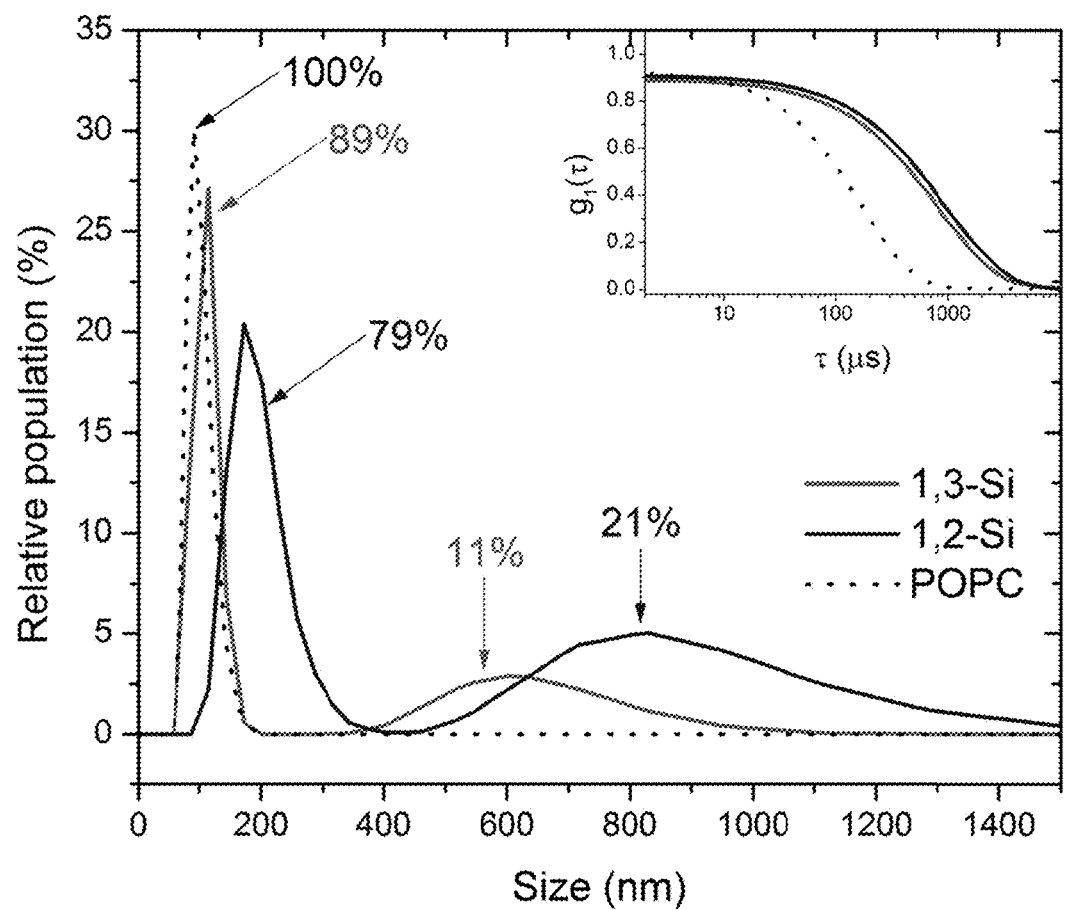
FIG. 5 shows particle size distribution, determined by dynamic light scattering (DLS), of POPC (black dotted line), 1,2-SiPC (darker grey solid line), and 1,3-SiPC (lighter grey solid line) liposomes as aqueous suspensions in exemplary and comparative embodiments of the present application. POPC ULVs contain 5 mol % of 1-palmitoyl-2-oleoyl-sn-3-glcyercophosphoglycerol (POPG) and were extruded through a 100 nm polycarbonate membrane. SiPC suspensions were not extruded. The inset shows representative autocorrelation functions for each species.

Liposome size was determined by DLS (FIG. 5) and is also summarized in Table 1. One size population was observed for POPC ULVs, having an average diameter of 98.1 nm. Two populations were observed for both of the SiPC liposomal preparations examined with the most populous vesicle diameter being 193.7 nm and 123.4 nm for 1,2-SiPC and 1,3-SiPC respectively. The diameter standard deviation (a) for the vesicles (most abundant population) was below 20% of the diameter for liposomes of 1,2-SiPC and 1,3-SiPC, thus implying very low polydispersities of 0.16 and 0.19 respectively.

The bilayer properties of vesicles produced from two siloxane-containing phosphocholines were examined. Through SAXS, liposomes of SiPCs bear a similarity to unsaturated phospholipids. Resulting from the presence of the trisiloxane moiety, the area per lipid and lipid volume values are slightly larger than physiologically relevant phosphocholines such as POPC despite the similar bilayer structure. Liposomes were prepared using only freeze-thaw cycles to give low dispersity suspensions and these properties make these lipids and their liposomes useful components of drug delivery preparations.

Example 3: Alternative Synthesis of Trisiloxane Phosphocholines

General Procedure: An example of an alternative synthetic strategy employed in the synthesis of siloxane phospholipids is shown in Scheme 3.

Scheme 3: Alternative synthetic strategy employed in the synthesis of siloxane phospholipids.

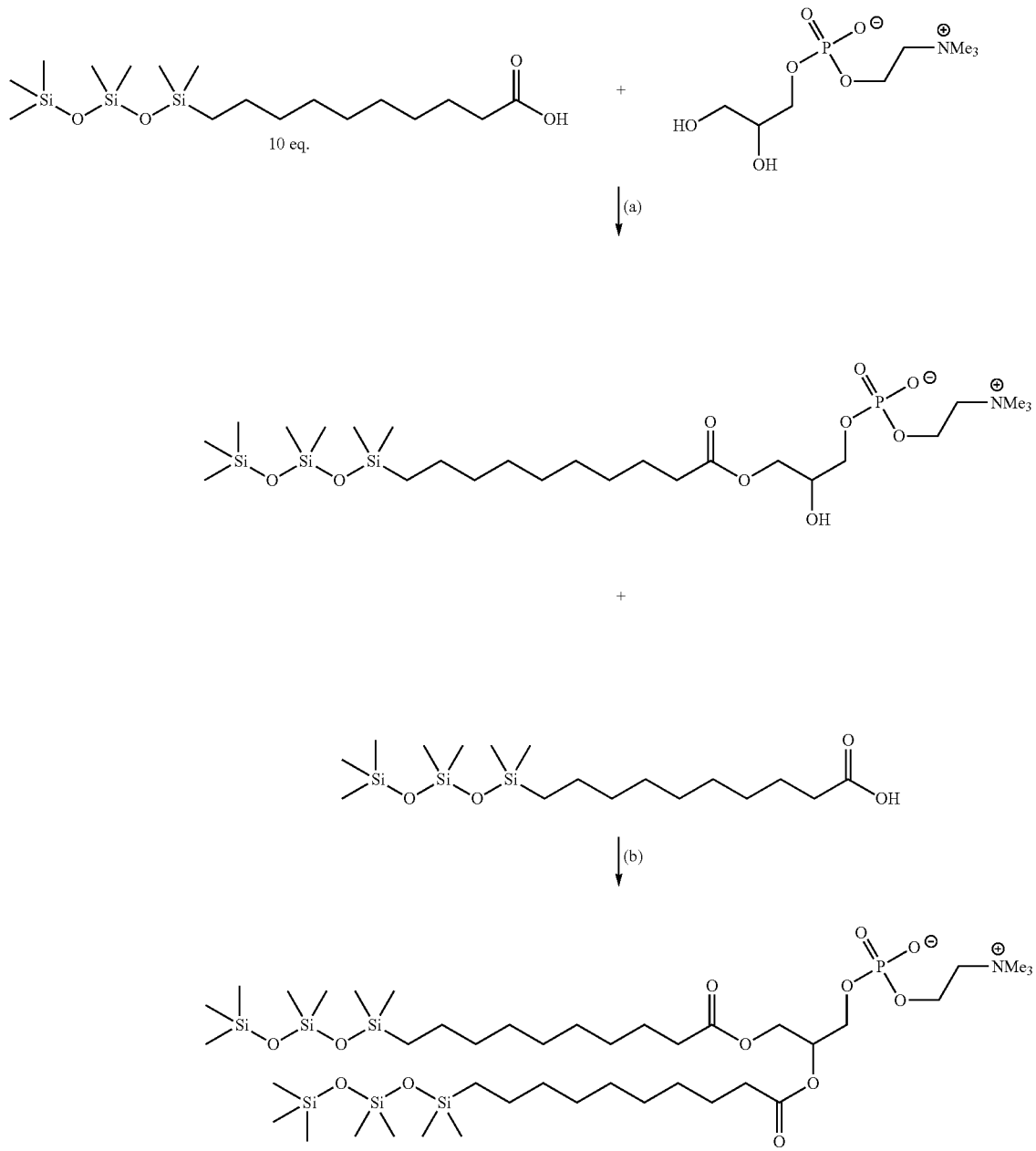

(a) N435, 65-80° C., 28.5 in Hg, 72 h; (b) DCC/DMAP, CHCl$_3$, N$_2$.

In the alternative synthetic strategy, a 25 ml Teflon round bottomed flask was charged with about 1 eq. of α-glycerophosphocholine and about 10 eq. of the siloxane-functionalized fatty acid and heated to 65° C. for 5 min with stirring. Immobilized lipase from *Candida antarctica* (N435) was added to the reaction mixture and stirred for 5 minutes, after which time a vacuum adaptor was connected and the pressure was reduced to 28.5 inHg. The reaction mixture was stirred for 48 h. Upon completion of the reaction the contents of the flask were cooled to room temperature and 10 mL of 9:1 chloroform:methanol was added to dilute. The contents were filtered through a medium porosity glass fritted Büchner funnel and the solvent was removed in vacuo. After column chromatography on silica gel using an isocratic elution solvent of 65:25:4 chloroform:methanol:water the desired intermediate was recovered as an opaque gel.

Intermediates having the following structures were prepared in accordance with the above general procedure:

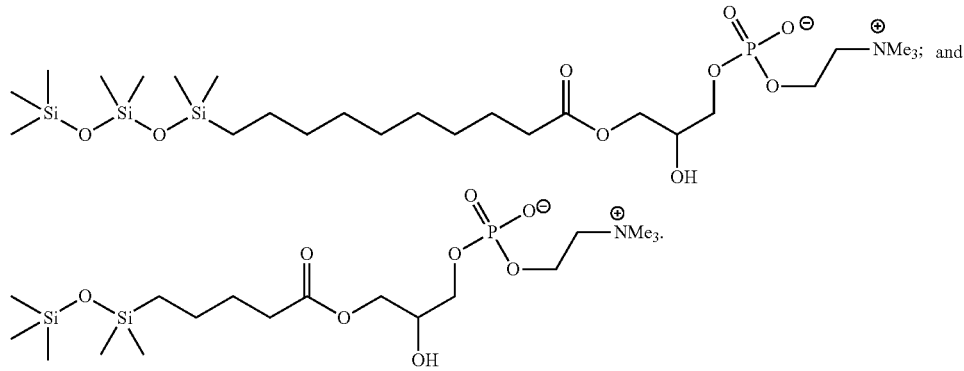

To obtain the siloxane-functionalized phospholipid, the intermediate was then reacted with another portion (10 eq.) of the siloxane-functionalized fatty acid under Steglich esterification conditions (DCC/DMAP, CHCl$_3$, N$_2$).

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1] W. Dowhan, M. Bogdanov, and E. Mileykovskaya, *Functional Roles of Lipids in Membranes*, in D. E. Vance and J. E. Vance (Eds.), *Biochemistry of Lipids, Lipoproteins, and Membranes* (5$^{th}$ Edition), Elsevier, The Netherlands, 2008.
[2] A. Shevchenko and K. Simons. *Nat. Rev. Mol. Cell Biol.*, 2010, 11, 593-598.
[3] V. P. Torchilin, *Nature Rev. Drug Discovery*, 2005, 4, 145.
[4] M. L. Blank, F. Snyder, L. W. Byers, B. Brooks, and E. Muirhead. *Biochem. Biophys. Res. Commun.*, 1979, 90, 1194-1200.
[5] D. R Hoffman, L. H. Hoffman, and F. Snyder. *Cancer Res.*, 1986, 46, 5803-5809.
[6] D. R. Hoffman, J. Hajdu, and F. Snyder. *Blood*, 1984, 63, 545-552.
[7] S. K. Bhatia and J. Hajdu. *J. Org. Chem.*, 1988, 53, 5034-5039.
[8] I. A. Fedotenko, P.-L. Zaffalon, F. Favarger, and A. Zumbuehl. *Tet. Lett.*, 2010, 51, 5382-5384.
[9] T. J. Macintosh, S. A. Simon, P. Vierling, C. Santaella, and V. Ravily. *Biophysical J.*, 1996, 71, 1853.
[10] L. Clary, G. Verderone, C. Santaella, P. Vierling, and P. Chang. *Chem. Phys. Lipids*, 1997, 86, 21.
[11] J. Guimond-Tremblay, M.-C. Gagnon, J.-A. Pineault-Maltais, V. Turcotte, M. Auger, and J.-F. Paquin. *Org. Biomol. Chem.*, 2012, 10, 1145.
[12] M.-C. Gagnon, B. Turgeon, J.-D. Savoie, J.-F. Parent, M. Auger, and J.-F. Paquin. *Org. Biomol. Chem.*, 2014, 12, 5126.
[13] T. Markowski, S. Drescher, G. Forster, B.-D. Lechner, A. Meister, A. Blume, and B. Dobner. *Langmuir*, 2015, 31, 10683-10692.
[14] M. Wang, S. Pinnamaraju, R. Ranganathan, and J. Hajdu. *Chem. Phys. Lipids*, 2013, 172-173, 78-85.
[15] R. Krishnamohanrao, U. J. Krull, and M. Thompson. *J. Org. Chem.*, 1987, 52, 5478.
[16] M.-P. Nieh, J. Katasaras, and X. Qi. *Biochim. Biophys. Acta*, 2008, 1778, 1467.
[17] L. Clary, G. Verderone, C. Santaella, P. Vierling, and P. Chang. *Chem. Phys. Lipids*, 1997, 86, 21; M.-P. Nieh, J. Katsaras, and X. Qi. *Biochim. Biophys. Acta*, 2008, 1778, 1467; M.-P. Nieh, T. A. Harroun, V. A. Raghunathan, C. J. Glinka, and J. Katsaras. *Biophys. J.*, 2004, 86, 2615; B. Yue, C.-Y. Huang, M.-P. Nieh, C. J. Glinka, and J. Katsaras. *J. Phys. Chem. B.*, 2005, 109, 609; M. Hashida, S. Kawakami, and F. Yamashita. *Chem. Pharm. Bull.*, 2005, 53, 871.
[18] See for example, Pattmi, B. S. et al. *Chemical Reviews*, 2015, 115(19), 10938-10966; Kaur, L. et al. *IJRPC*, 2013, 3(1), 121-128.
[19] L. Zhu, D. Gregurec, I. Reviakine (2013) Nanoscale departures: excess lipid leaving the surface during supported lipid bilayer formation, *Langmuir*, 29, 15283-15292.
[20] See for example: Ruysschaert, T., et al. *BMC Biotechnology*, 2005, 5(11), 1-13.
[21] M. B. Frampton and P. M. Zelisko. *Enz. Microbiol. Technol.*, 2014, 58-59, 87-92.
[22] M. B. Frampton, P. M. Zelisko (2014), Chain length selectivity during the polycondensation of siloxane-containing esters and alcohols by immobilized *Candida antarctica* lipase B, *Enzyme & Microbial Technology*, 58-59, 87-92.

23. I. Karabulut, G. Durmaz, and A. A. Hayaloglu. *J. Agric. Food Chem.*, 2009, 57, 7584-7590.
24. Q. Lei, W. L. Lee, and T. Li. *Eur. J. Lipid Sci. Technol.*, 2013, 115, 232-238.
25. U. T. Kim and J. Hajdu. *J. Chem. Soc., Chem. Commun.*, 1993, 70-71.
26. Blanchet, C. E., Spilotros, A., Schwemmer, F., Graewert, M. A., Kikhney, A., Jeffries, C. M., Franke, D., Mark, D., Zengerle, R., Cipriani, F., Fiedler, S., Roessle, M. & Svergun, D. I. (2015). *J. Appl. Cryst.* 48, 431-443.
27. M. V. Petoukhov, D. Franke, A. V. Shkumatov, G. Tria, A. G. Kikhney, M. Gajda, C. Gorba, H. D. T Mertens, P. V. Konarev, P. V. and D. I. Svergun. *J. of Appl. Cryst.*, 2012, 45, 342.
28. G. Pabst, M. Rappolt, H. Amenitsch and P. Laggner. *Phys. Rev. E.*, 2000, 62, 4000.
29. N. Kucerka, M-P. Nieh, and J. Katsaras. *Biochim. Biophys. Acta*, 2011, 1808, 2761.
30. M. V. Petoukhov, D. Franke, A. V. Shkumatov, G. Tria, A. G. Kikhney, M. Gajda, C. Gorba, H. D. T Mertens, P. V. Konarev, P. V. and D. I. Svergun. *J. of Appl. Cryst.*, 2012, 45, 342.
31. G. Pabst, M. Rappolt, H. Amenitsch and P. Laggner. *Phys. Rev. E.*, 2000, 62, 4000.
32. Nagle, J. F.; Wiener, M. C. (1988): Structure of fully hydrated bilayer dispersions. In *Biochimica et Biophysica Acta (BBA)—Biomembranes* 942 (1), pp. 1-10. DOI: 10.1016/0005-2736(88)90268-4.
33. Nagle, John F.; Tristram-Nagle, Stephanie (2000): Structure of lipid bilayers. In Biochimica et Biophysica Acta (BBA)—Reviews on Biomembranes 1469 (3), pp. 159-195. DOI: 10.1016/S0304-4157(00)00016-2.
34. N. Kucerka, M-P. Nieh, and J. Katsaras. *Biochim. Biophys. Acta*, 2011, 1808, 2761.
35. Daniela Uhríková, Peter Rybár, Tibor Hianik, Pavol Balgavý, Component volumes of unsaturated phosphatidylcholines in fluid bilayers: a densitometric study, Chemistry and Physics of Lipids, Volume 145, Issue 2, February 2007, 97-105.
36. J. B. Klauda, V. Monje, T. Kim, and W. Im. *J. Phys. Chem. B.*, 2012, 116, 9424.

TABLE 1

| Structural parameters derived from experimental SAXS and DLS data. | | | |
|---|---|---|---|
| | POPC | 1,2-SiPC | 1,3-SiPC |
| Fit Parameters | | | |
| $\bar{\rho}_H$ (e/Å$^3$) | 0.1609$^a$ | 0.1609$^a$ | 0.1609$^a$ |
| $\bar{\rho}_C$ (e/Å$^3$) | −0.152 ± 0.002 | −0.106 ± 0.002 | −0.101 ± 0.003 |
| $z_H$ (Å) | 18.16 ± 0.08 | 18.2 ± 0.05 | 17.6 ± 0.1 |
| $\sigma_H$ (Å) | 3.77 ± 0.06 | 4.6 ± 0.1 | 4.3 ± 0.2 |
| $\sigma_C$ (Å) | 6.9 ± 0.2 | 14.1 ± 0.2 | 13.3 ± 0.3 |
| Geometrically Derived Parameters | | | |
| $d_H$ (Å) | 7.5 ± 0.2 | 9.1 ± 0.3 | 8.6 ± 0.5 |
| $d_C$ (Å) | 14.4 ± 0.1 | 9.9 ± 0.5 | 13.2 ± 0.2 |
| $d_B$ (Å) | 43.7 ± 0.2 | 45.5 ± 0.3 | 43.9 ± 0.4 |
| $d_{HH}$ (Å) | 36.3 ± 0.1 | 36.3 ± 0.1 | 35.3 ± 0.1 |
| $A_L$ (Å$^2$) | 58.9 ± 2 | 69 ± 2 | 72 ± 4 |
| $V_C$ (Å$^3$) | 961 ± 27 | 1243 ± 42 | 1246 ± 81 |
| $V_H$ (Å$^3$) | 331$^a$ | 331$^a$ | 331$^a$ |
| DLS$^b$ Parameters | | | |
| Dia. (nm) | 98.1 | 193.7 | 123.4 |
| σ (nm) | 10.6 | 31.9 | 23.5 |
| Rel. pop. | 100% | 79% | 89% |

TABLE 1-continued

| Structural parameters derived from experimental SAXS and DLS data. | | | |
|---|---|---|---|
| | POPC | 1,2-SiPC | 1,3-SiPC |
| Dia. (nm) | — | 949.8 | 684.9 |
| σ (nm) | — | 62.0 | 62.1 |
| Rel. pop. | — | 21% | 11% |

$^a$Fixed using experimentally determined volume.$^{29}$
$^b$Dynamic light scattering.

20. The compound of claim 19, wherein the compound is:
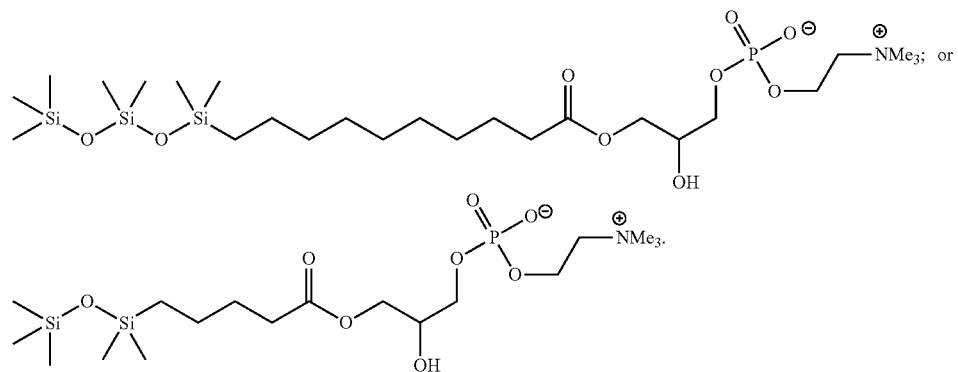

The invention claimed is:

1. A compound of formula I:

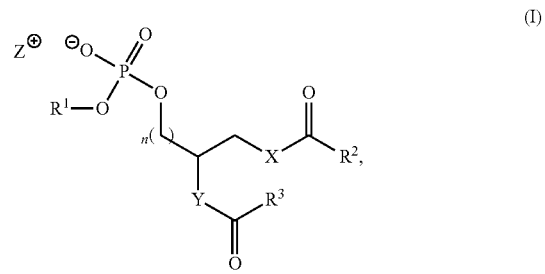

(I)

wherein
R$^1$ is a phospholipid head group;
R$^2$ and R$^3$ are independently selected from C$_{2-30}$alkylene-A and C$_{2-30}$alkenylene-A;
A has the structure:

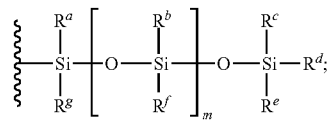

R$^a$, R$^b$, R$^c$, R$^d$, R$^e$, R$^f$ and R$^g$ are independently selected from C$_{1-6}$alkyl, C$_{3-10}$cycloalkyl, C$_{1-6}$alkyleneC$_{6-10}$aryl and C$_{6-10}$aryl;
m is an integer of from 0 to 20;
n is 0 or 1;
X is selected from O and NR$^4$;
Y is selected from O, NR$^4$ and CH$_2$—O;
R$^4$ is H or C$_{1-4}$alkyl; and
Z$^+$ is a counter cation or Z$^+$ is not present when R$^1$ is a phospholipid head group comprising a counter cation.

2. The compound of claim 1, wherein R$^1$ is choline.
3. The compound of claim 1, wherein R$^2$ and R$^3$ are independently C$_{2-10}$alkylene-A.
4. The compound of claim 1, wherein R$^a$, R$^b$, R$^c$, R$^d$, R$^e$, R$^f$ and R$^g$ are each methyl.
5. The compound of claim 1, wherein m is 1.
6. The compound of claim 1, wherein X is O.
7. The compound of claim 1, wherein Y is O.
8. The compound of claim 1, wherein Y is CH$_2$—O.
9. The compound of claim 1, wherein Z$^+$ is an inorganic species that is a metal.
10. The compound of claim 1, wherein Z$^+$ is an organic species.
11. The compound of claim 1, wherein R$^1$ comprises a counter cation and Z$^+$ is not present.
12. The compound of claim 1, wherein the compound has the structure:

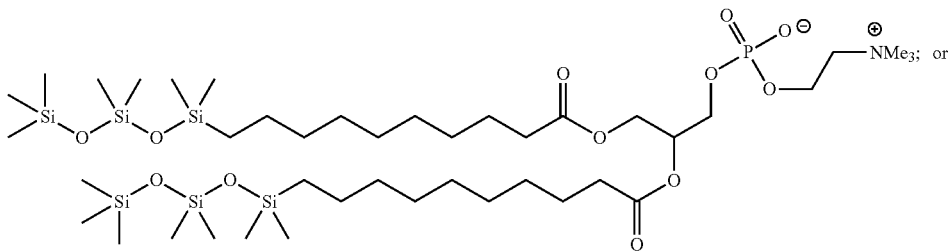

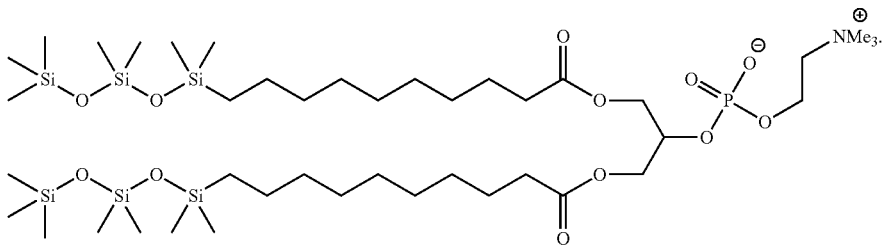

13. Liposomes comprising one or more compounds of claim 1.

14. The liposomes of claim 13, wherein the compounds have the structure:

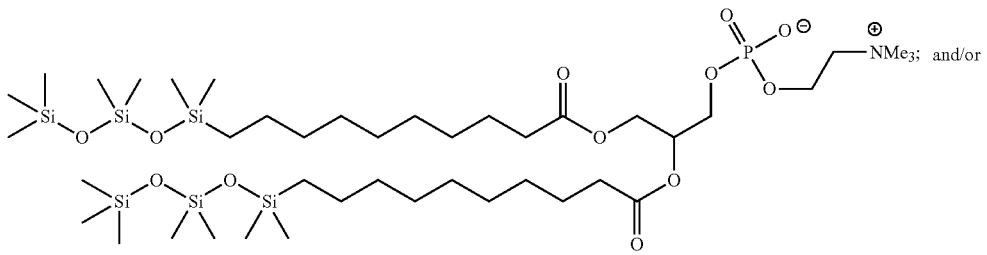

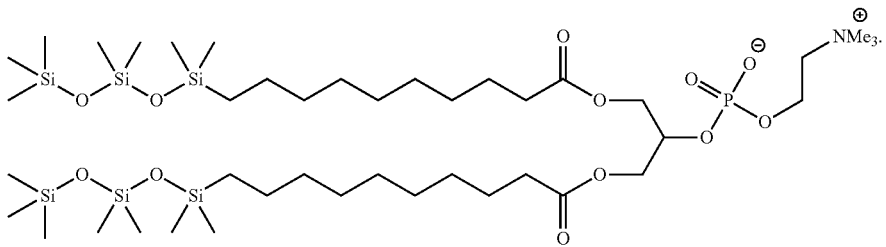

15. The liposomes of claim 13, wherein the liposomes are unilamellar.

16. A fast-encapsulation drug delivery system comprising the liposomes of claim 13.

17. A pharmaceutical composition comprising the liposomes of claim 13, and a pharmaceutically acceptable carrier.

18. A method of delivering an active agent to a subject in need of treatment with the active agent comprising administering an effective amount of the liposomes of claim 13 to said subject, wherein the liposomes comprise the active agent.

19. A compound of Formula (IV):

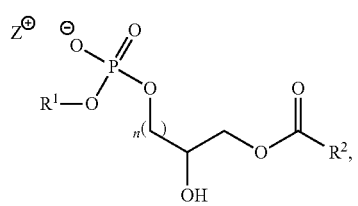

(IV)

wherein $R^1$, $R^2$, n and $Z^+$ are as defined in claim 1.